(12) United States Patent
Arber Barth et al.

(10) Patent No.: US 12,377,147 B2
(45) Date of Patent: Aug. 5, 2025

(54) REPROGRAMMING CD4 T CELLS INTO CYTOTOXIC CD8 CELLS BY FORCED EXPRESSION OF CD8ab AND CLASS 1 RESTRICTED T CELL RECEPTORS

(71) Applicant: Baylor College of Medicine, Houston, TX (US)

(72) Inventors: Caroline Eva Arber Barth, Houston, TX (US); Gagan Bajwa, Houston, TX (US); Malcolm K. Brenner, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 1179 days.

(21) Appl. No.: 17/048,490

(22) PCT Filed: Apr. 18, 2019

(86) PCT No.: PCT/US2019/028202
§ 371 (c)(1),
(2) Date: Oct. 16, 2020

(87) PCT Pub. No.: WO2019/204662
PCT Pub. Date: Oct. 24, 2019

(65) Prior Publication Data
US 2021/0361705 A1 Nov. 25, 2021

Related U.S. Application Data

(60) Provisional application No. 62/659,971, filed on Apr. 19, 2018.

(51) Int. Cl.
*A61K 35/00* (2006.01)
*A61K 40/11* (2025.01)
*A61K 40/32* (2025.01)
*A61K 40/42* (2025.01)
*A61K 45/06* (2006.01)
*A61K 48/00* (2006.01)
*A61P 35/00* (2006.01)
*C07K 14/47* (2006.01)
*C07K 14/705* (2006.01)
*C07K 14/725* (2006.01)
*C12N 5/0783* (2010.01)

(52) U.S. Cl.
CPC .............. *A61K 45/06* (2013.01); *A61K 40/11* (2025.01); *A61K 40/32* (2025.01); *A61K 40/424* (2025.01); *A61P 35/00* (2018.01); *C07K 14/4748* (2013.01); *C07K 14/7051* (2013.01); *C07K 14/70517* (2013.01); *C12N 5/0638* (2013.01); *A61K 2239/31* (2023.05); *A61K 2239/38* (2023.05); *A61K 2239/48* (2023.05); *C12N 2510/00* (2013.01)

(58) Field of Classification Search
CPC ......... A61K 35/17; A61K 45/06; A61P 35/00; C07K 14/4748; C07K 14/7051; C07K 14/70517; C12N 5/0638; C12N 2510/00
See application file for complete search history.

(56) References Cited

U.S. PATENT DOCUMENTS

| | | | |
|---|---|---|---|
| 4,870,287 A | 9/1989 | Cole et al. | |
| 5,348,878 A | 9/1994 | Rock | |
| 5,739,169 A | 4/1998 | Ocain et al. | |
| 5,760,395 A | 6/1998 | Johnstone | |
| 5,801,005 A | 9/1998 | Cheever et al. | |
| 5,824,311 A | 10/1998 | Greene et al. | |
| 5,830,880 A | 11/1998 | Sedlacek et al. | |
| 5,846,945 A | 12/1998 | Mccormick | |
| 6,410,319 B1 | 6/2002 | Raubitschek et al. | |
| 6,544,518 B1 | 4/2003 | Friede et al. | |
| 7,109,304 B2 | 9/2006 | Hansen et al. | |
| 10,538,574 B2 | 1/2020 | Bleakley et al. | |
| 10,918,665 B2 * | 2/2021 | Brentjens | A61K 39/464412 |
| 10,975,137 B2 | 4/2021 | Davila | |
| 11,034,748 B2 | 6/2021 | Chapuis | |
| 11,236,166 B2 * | 2/2022 | Kley | C07K 16/2887 |
| 11,446,398 B2 | 9/2022 | Barrett et al. | |
| 11,648,268 B2 | 5/2023 | Adusumilli | |
| 11,661,455 B2 | 5/2023 | Tavernier et al. | |

(Continued)

FOREIGN PATENT DOCUMENTS

| | | |
|---|---|---|
| EP | 2408934 B1 | 11/2014 |
| JP | 2018517674 A | 7/2018 |

(Continued)

OTHER PUBLICATIONS

Xue et al (OncoImmunology 2:1, e22590, publication Oct. 18, 2012) (Year: 2012).*
Okamoto et al (Molecular Therapy—Nucleic Acids (2012) 1, e63, publication Dec. 18, 2012) (Year: 2012).*
Xue et al (Oncoimmunology 2: 1 e22590, Jan. 2013 (Year: 2013).*
Xue et al (Haematologica 95: 126-134, 2010 (Year: 2010).*
Xue, et al., "Human MHC Class I-restricted high avidity CD4+ T cells generated by co-transfer of TCR and CD8 mediate efficient tumor rejection in vivo," Oncoimmunology, (2013), vol. 2, No. 1, pp. e22590:1-12.

(Continued)

*Primary Examiner* — Lei Yao
(74) *Attorney, Agent, or Firm* — McBee Moore & Vanik IP, LLC

(57) ABSTRACT

Embodiments of the disclosure include methods and compositions related to improvements of T cell therapy. In particular embodiments, CD8+ T cell therapy is enhanced upon expression of transgenic E08αβ co-receptor in the CD8+ T cells. In certain embodiments, CD4+ T cells are rendered to have cytotoxic cell function for adoptive transfer upon expression of transgenic E08αβ co-receptor in the CD4+ T cells. In specific embodiments, TCR-expressing and E08αβ co-receptor-expressing CD4+ and CD8+ T cells are utilized in adoptive transfer.

14 Claims, 9 Drawing Sheets

Specification includes a Sequence Listing.

(56) References Cited

U.S. PATENT DOCUMENTS

| | | |
|---|---|---|
| 2002/0155604 A1 | 10/2002 | Ledbetter et al. |
| 2003/0118592 A1 | 6/2003 | Ledbetter |
| 2005/0118676 A1 | 6/2005 | Qi |
| 2005/0260186 A1 | 11/2005 | Bookbinder et al. |
| 2006/0067920 A1* | 3/2006 | Jensen ............... C07K 14/5437 |
| 2006/0104968 A1 | 5/2006 | Bookbinder et al. |
| 2007/0209083 A1 | 9/2007 | Thiam |
| 2009/0053249 A1 | 2/2009 | Qi |
| 2011/0065779 A1 | 3/2011 | Fang et al. |
| 2013/0336922 A1* | 12/2013 | Weinschenk ............ A61P 35/04 424/85.1 |
| 2016/0002612 A1* | 1/2016 | Gerometta ............... C12N 9/12 435/69.6 |
| 2017/0240884 A1 | 8/2017 | Dornmair et al. |
| 2018/0084768 A1 | 3/2018 | Macdonald et al. |
| 2021/0317184 A1 | 10/2021 | Brett |
| 2021/0361705 A1 | 11/2021 | Arber Barth |
| 2024/0050570 A1 | 2/2024 | Melchiori |
| 2024/0279307 A1 | 8/2024 | Bleakley |
| 2024/0374728 A1 | 11/2024 | Melchiori |

FOREIGN PATENT DOCUMENTS

| | | |
|---|---|---|
| JP | 2020-509767 A | 4/2020 |
| WO | 99/40188 A2 | 8/1999 |
| WO | 2014/055668 A1 | 4/2014 |
| WO | 201490985 A1 | 6/2014 |
| WO | 2017/075389 A1 | 5/2017 |
| WO | 2018/058002 A1 | 3/2018 |
| WO | 201858002 A1 | 3/2018 |
| WO | 2018/161064 A1 | 9/2018 |
| WO | 2018/170338 A2 | 9/2018 |
| WO | 2019/028295 A1 | 2/2019 |
| WO | 2019204662 A1 | 10/2019 |
| WO | 2020049496 A1 | 3/2020 |
| WO | 2020109616 A1 | 6/2020 |

OTHER PUBLICATIONS

Chua, Ignatius Chung, "CD8 co-receptor modifications to enhance T cell immunotherapy," Thesis submitted to the Division of Infection and Immunity of UCL, (2013), Chapters 3.3, 5.3.3, 6.2; Discussion at pp. 159-160; Figures 3-9 to 3-10, 3-17, 5-10 to 5-12, 5-15, 6-4 to 6-5.

Second Third party Observation for application No. EP20190789197, submitted Oct. 31, 2022.

Arber, Caroline, et al. "Survivin-specific T cell receptor targets tumor but not T cells" The Journal of Clinical Investigation, vol. 125, No. 1, pp. 157-168, Jan. 2015.

Bennekov, Thomas, et al. "Induction of immunity against human cytomegalovirus" Mt. Sinai Journal of Medicine, vol. 71, No. 2, pp. 86-93, Mar. 2004 (Abstract Only).

Cameron, Brian J., et al. "Identification of a Titin-derived HLA-A1-presented peptide as a cross-reactive target for engineered MAGE A3-directed T cells" Science Translational Medicine, vol. 5, No. 197, Aug. 2013.

Cho, Jae-Ho, et al. "TCR tuning of T cell subsets" Immunological Reviews, vol. 283, No. 1, pp. 129-137, May 2018.

Cole, David K., et al. "The molecular determinants of CD8 co-receptor function" Immunology, vol. 137, No. 2, pp. 139-148, Oct. 2012.

Fast, Loren D., et al. "Inhibition of xenogeneic GVHD by PEN110 treatment of donor human PBMNCs" Transfusion Complications, vol. 44, Issue 2, pp. 282-285, Feb. 2004.

Frankel, Timothy L., et al. "Both CD4 and CD8 T cells mediate equally effective in vivo tumor treatment when engineered with a highly avid TCR targeting tyrosinase" The Journal of Immunology, vol. 184, No. 11, pp. 5988-5998, Jun. 2010.

Frolet, Cecile, et al. "New adhesin functions of surface-exposed pneumococcal proteins" BMC microbiology, vol. 10, No. 1, pp. 1-3, Dec. 2010.

Gundry, Michael C., et al. "Highly efficient genome editing of murine and human hematopoietic progenitor cells by CRISPR/Cas9" Cell Reports, vol. 17, No. 5, pp. 1453-1461, Oct. 2016.

Hebeisen, Michael, et al. "Identifying individual T cell receptors of optimal avidity for tumor antigens" Frontiers in Immunology, vol. 6, Article 582, Nov. 18, 2015.

Hebeisen, Michael, et al. "Identification of Rare High-Avidity, Tumor-Reactive CD8+ T Cells by Monomeric TCR-Ligand Off-Rates Measurements on Living Cells" Cancer Research, vol. 75, No. 10, pp. 1983-1991, May 2015.

International Search Report and Written Opinion mailed Jul. 22, 2019 in International Application No. PCT/US2019/028202 (14 pages).

Kabouridis, Panagiotis S. "Lipid rafts in T cell receptor signalling" Molecular Membrane Biology, vol. 23, No. 1, pp. 49-57, Jan. 2006.

Kennedy, Richard, et al. "Multiple roles for CD4+ T cells in anti-tumor immune responses" Immunological Reviews, vol. 222, No. 1, pp. 129-144, Apr. 2008.

Kessels, Helmut W.H.G., et al. "Generation of T Cell Help through a MHC Class I-Restricted TCR1" The Journal of Immunology, vol. 177, pp. 976-982, 2006.

Laugel, Bruno, et al. "The multiple roles of the CD8 coreceptor in T cell biology: opportunities for the selective modulation of self-reactive cytotoxic T cells" Journal of Leukocyte Biology, vol. 90, No. 6, pp. 1089-1099, Dec. 2011.

Leisegang, Matthias, et al. "MHC-restricted fratricide of human lymphocytes expressing survivin-specific transgenic T cell receptors" The Journal of Clinical Investigation, vol. 120, No. 11, pp. 3869-3877, Nov. 2010.

Li, Yi, et al. "Directed evolution of human T-cell receptors with picomolar affinities by phage display" Nature Biotechnology, vol. 23, No. 3, pp. 349-354, Mar. 2005.

Liadi, Ivan, et al. "Individual Motile CD4+ T Cells Can Participate in Efficient Multikilling through Conjugation to Multiple Tumor Cells" Cancer Immunology Research, vol. 3, No. 5, pp. 473-482, May 2015.

Linette, Gerald P., et al. "Cardiovascular toxicity and titin cross-reactivity of affinity-enhanced T cells in myeloma and melanoma" Blood, The Journal of the American Society of Hematology, vol. 122, No. 6, pp. 863-871, Aug. 2013.

Linnemann, Carsten, et al. "High-throughput epitope discovery reveals frequent recognition of neo-antigens by CD4+ T cells in human melanoma" Nature Medicine, vol. 21, No. 1, pp. 81-85, Jan. 2015.

Lockey, Td, et al. "Epstein-Barr virus vaccine development: a lytic and latent protein cocktail" Frontiers in Bioscience-Landmark, vol. 13, No. 15, pp. 5916-5927, May 2008.

Loewendorf, A., et al. "Modulation of host innate and adaptive immune defenses by cytomegalovirus: timing is everything" Journal of Internal Medicine, vol. 267, No. 5, pp. 483-501, May 2010.

Merouane, Amine, et al. "Automated profiling of individual cell-cell interactions from high-throughput time-lapse maging microscopy in nanowell grids (TIMING)" Bioinformatics, vol. 31, No. 19, pp. 3189-3197, Oct. 2015.

Morgan, Richard A., et al. "Cancer regression in patients after transfer of genetically engineered lymphocytes" Science, vol. 314, No. 5796, pp. 126-129, Oct. 2006.

Morgan, Richard A., et al. "Cancer regression and neurological toxicity following anti-MAGE-A3 TCR gene therapy" Journal of Immunotherapy, vol. 36, No. 2, pp. 133-151, Feb. 2013.

Morris, Emma C., et al. "A critical role of T cell antigen receptor-transduced MHC class I-restricted helper T cells In tumor protection" PNAS, vol. 102, No. 22, pp. 7934-7939, May 31, 2005.

Nishimura, Christopher D., et al. "c-MPL provides tumor-targeted T-cell receptor-transgenic T cells with costimulation and cytokine signals" Blood, The Journal of the American Society of Hematology, vol. 130, No. 25, pp. 2739-2749, Dec. 2017.

Ostroumov, D., et al. "CD4 and CD8 T lymphocyte interplay in controlling tumor growth" Cellular and molecular life sciences, vol. 75, No. 4, pp. 689-713, Feb. 2018.

Rapoport, A.P., et al. "NY-ESO-1-specific TCR-engineered T cells mediate sustained antigen-specific antitumor effects in myeloma" Nature Medicine, vol. 21, No. 8, pp. 914-921, Aug. 2015.

(56) References Cited

OTHER PUBLICATIONS

Ray, S., et al. "MHC-I-restricted melanoma antigen specific TCR-engineered human CD4+ T cells exhibit multifunctional effector and helper responses, in vitro" Clinical Immunology, vol. 136, No. 3, pp. 338-347, Sep. 2010.
Robbins, Pf, et al. "Tumor regression in patients with metastatic synovial cell sarcoma and melanoma using genetically engineered lymphocytes reactive with NY-ESO-1" Journal of Clinical Oncology. Mar. 3, 2011;29(7):917.
Robbins, Pf, et al. "Single and dual amino acid substitutions in TCR CDRs can enhance antigen-specific T cell functions". The Journal of Immunology. May 1, 2008;180(9):6116-31.
Romain, G, et al. "Antibody Fc engineering improves frequency and promotes kinetic boosting of serial killing mediated by NK cells" Blood, The Journal of the American Society of Hematology. Nov. 20, 2014;124(22):3241-9.
Rieder, Mark J., et al. "Sequence variation in the human angiotensin converting enzyme" Nature Genetics, vol. 22, pp. 59-62, May 1999.
Ryckman, Brent J., et al. "Human Cytomegalovirus Entry into Epithelial and Endothelial Cells Depends on Genes UL128 to UL150 and Occurs by Endocytosis and Low-pH Fusion" Journal of Virology, vol. 80, No. 2, pp. 710-722, Jan. 2006.
Snyder, Sa, et al. "Role of membranes and activated carbon in the removal of endocrine disruptors and pharmaceuticals" Desalination. Jan. 5, 2007;202(1-3):156-81.
Sommermeyer, D, et al. "Chimeric antigen receptor-modified T cells derived from defined CD8+ and CD4+ subsets confer superior antitumor reactivity in vivo" Leukemia. Feb. 2016;30(2):492-500.
Thomas, Marco, et al. "Cytomegaloviral protein kinase pUL97 interacts with the nuclear mRNA export factor pUL69 to modulate its intranuclear localization and activity" Journal of General Virology, vol. 90, pp. 567-578, 2009.
Tran, E., "Cancer immunotherapy based on mutation-specific CD4+ T cells in a patient with epithelial cancer" Science, May 9, 2014;344(6184):641-5.
Turtle, Cj, et al. "Immunotherapy of non-Hodgkin's lymphoma with a defined ratio of CD8+ and CD4+ CD19-specific chimeric antigen receptor-modified T cells" Science translational medicine. Sep. 7, 2016;8(355):355ra116-.
Provisional U.S. Appl. No. 62/769,405, filed Nov. 19, 2018.
Provisional U.S. Appl. No. 62/773,372, filed Nov. 30, 2018.
Provisional U.S. Appl. No. 62/791,464, filed Jan. 11, 2019.
Walter, Ea, et al. "Reconstitution of cellular immunity against cytomegalovirus in recipients of allogeneic bone marrow by transfer of T-cell clones from the donor" New England Journal of Medicine. Oct. 1, 19959;333(16):1038-44.
Willemsen, R., et al. "Redirecting human CD4+ T lymphocytes to the MHC class I-restricted melanoma antigen MAGE-A1 by TCR ab gene transfer requires CD8a" Gene Therapy, vol. 12, pp. 140-146, 2005.
Ghorashian et al. "CD8 T Cell Tolerance to a Tumor-Associated Self-Antigen Is Reversed by CD4 T Cells Engineered To Express the Same T Cell Receptor" The Journal of Immunology. Feb. 1, 2015, vol. 194, No. 3, pp. 1080-1089.

Stone et al. "Opposite Effects of Endogenous Peptide-MHC Class I on T Cell Activity in the Presence and Absence of COB" The Journal of Immunology. May 1, 2011, vol. 186, No. 9, pp. 5193-5200.
Third party Observation for application No. EP20190789197, submitted Oct. 19, 2022.
Xue et al., "Human MHC Class I-restrcited high avidity CD4 T Cells generated by co-transfer of TCR and CD8 mediate efficient tumor rejection in vivo," Oncoimmunology, vol. 2, No. 1, pp. e22590: 1-12, Jan. 1, 2013.
Unitprot, P01732—CD8A_HUMAN, and first entry of the sequence into public domain (1988), 12 pages, Retrieved on Jun. 7, 2023 from URL: https://www.uniprot.org/uniprotkb/P01732/history.
NCBI GenBank BC100911.1, *Homo sapiens* CD8b molecule, mRNA (cDNA clone MGC:119114 IMAGE:40003720), complete cds, 2 pages, Retrieved on Jun. 7, 2023 from URL: https://www.ncbi.nlm.nih.gov/nuccore/BC100911.1?from=51&to=782.
NCBI GenBank: JA738613.1, Sequence 65 from Patent EP2408934, 1 page, Retrieved on Jun. 7, 2023 from URL: https://www.ncbi.nlm.nih.gov/nuccore/JA738613.1?from=51&to=782.
NCBI GenBank: LT736917.1, Human ORFeome Gateway entry vector pENTR223-CD8B, complete sequence, 2 pages, Retrieved on Jun. 7, 2023 from URL: https://www.ncbi.nlm.nih.gov/nuccore/LT736917.1?from=488&to=1218.
Voss et al., "Redirection of T Cells by Delivering a Transgenic Mouse-Derived MDM2 Tumor Antigen-Specific TCR and its Humanized Derivative Is Governed by the CD8 Coreceptor and Affects Natural Human TCR Expression," Immunologic Research, (2006), vol. 34, No. 1: 67-87.
Engels et al., "Redirecting T lymphocyte specificity by T cell receptor gene transfer—A new era for Immunotherapy," Molecular Aspects of Medicine, (2007), vol. 28, No. 1: 115-142.
Gangadharan et al., "The CD8 isoform CD8αα is not a functional homologue of the TCR co-receptor CD8αβ," Current Opinion in Immunology, (2004), vol. 16, No. 3: 264-270.
GenBank Accession No. MN366105.1; "Synthetic construct 11D5-3-CD8BBZ gene, complete cds"; (retrieved Dec. 4, 2020).
GenBank Accession No. MN366106.1; "Synthetic construct FHVH33-CD828Z gene, complete cds"; (retrieved Dec. 4, 2020).
GenBank Accession No. MN366107.1; "Synthetic construct FHVH33-CD8BBZ gene, complete cds"; (retrieved Dec. 4, 2020).
GenBank Accession No. MN698642.1; "Synthetic construct Hu19-CD828Z gene, complete cds"; (retrieved Dec. 4, 2020).
GenBank Accession No. MN702884.1; "Synthetic construct FMC63-CD828Z gene, complete cds"; (retrieved Dec. 4, 2020).
GenBank Accession No. MW218436.1; "Synthetic construct IC9-Luc90-CD828Z gene, complete cds"; (retrieved Dec. 4, 2020).
GenPept << T-cell surface glycoprotein CD8 alpha chain isoform 1 precursor [*Homo sapiens*] >>, NCBI Reference Sequence NP_001139345.1 (retrieved Dec. 4, 2020).
Xue et al., "Elimination of human leukemia cells in NOD/SCID mice by WT1-TCR gene transduced human T cells," Blood 106: 3062-3067 (Jul. 14, 2005).

\* cited by examiner

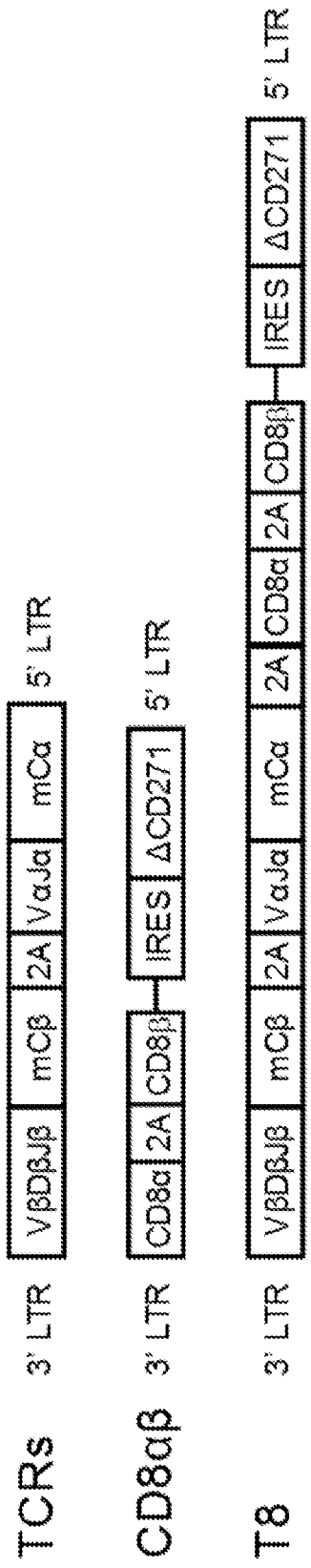
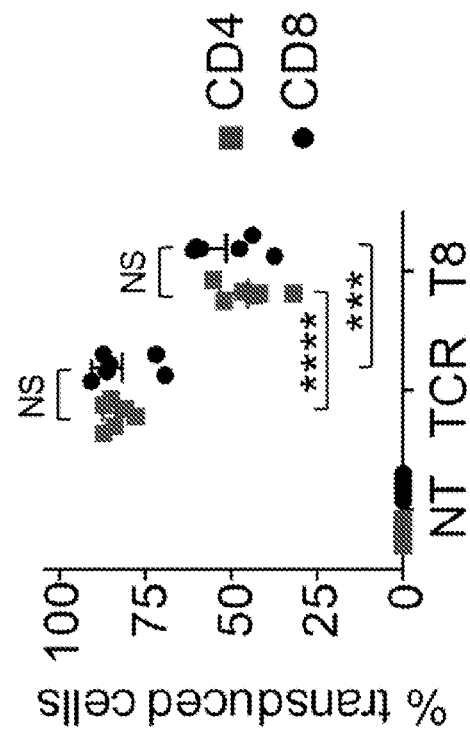
FIG. 1A
FIG. 1B

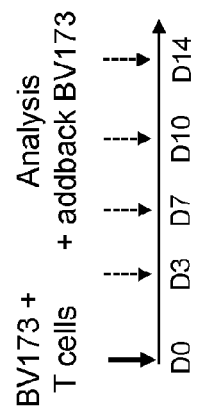
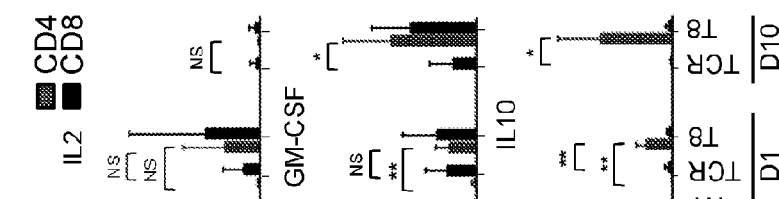
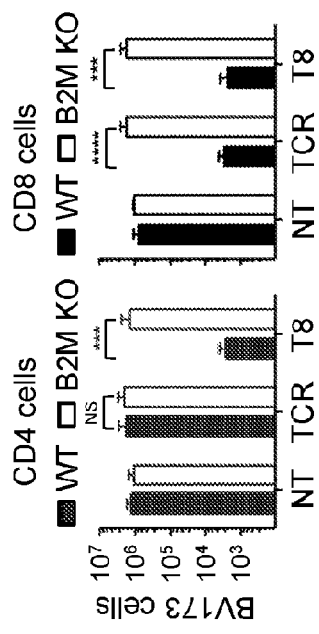
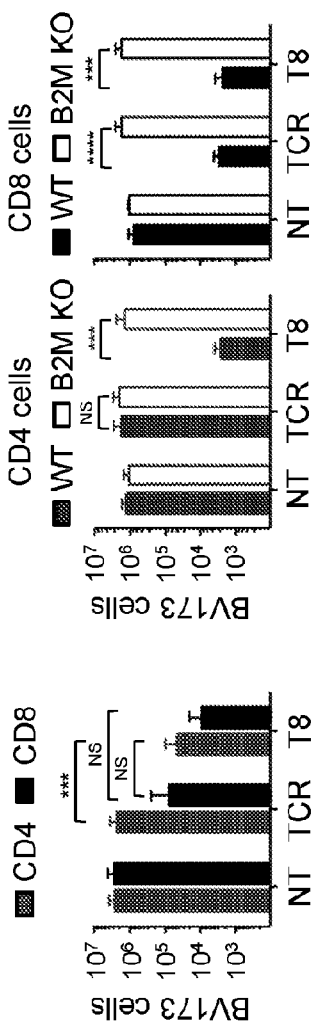
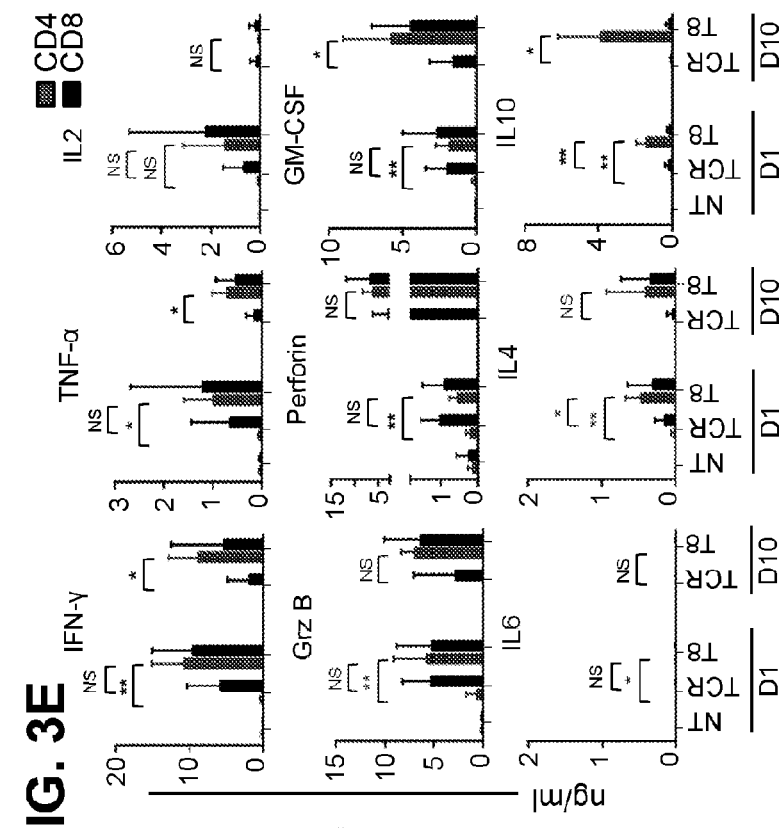
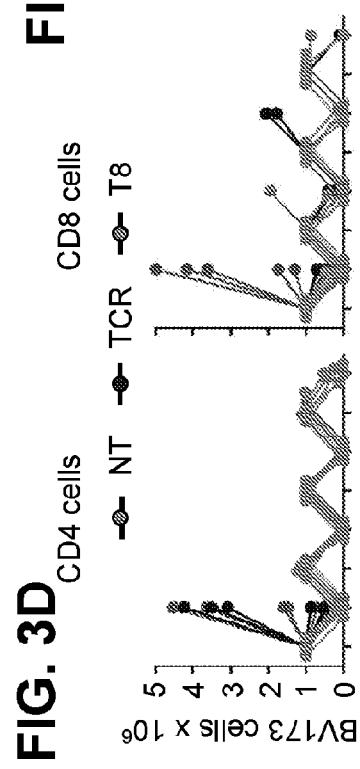

SEQUENCE LISTING

```
<160> NUMBER OF SEQ ID NOS: 14

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggccacggag cgagacaucu                                                   20

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Leu Thr Leu Gly Glu Phe Leu Lys Leu
1               5                   10

<210> SEQ ID NO 3
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Leu Thr His Val Leu Tyr Pro Val
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Met Leu Gly Glu Phe Leu Lys Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Leu Thr His Val Leu Tyr Pro Val
1               5

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may or may not be present

<400> SEQUENCE: 6

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may or may not be present

<400> SEQUENCE: 7

Gly Ser Gly Ala Thr Asn Phe Ser Leu Leu Lys Gln Ala Gly Asp Val
1               5                   10                  15
```

Glu Glu Asn Pro Gly Pro
            20

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may or may not be present

<400> SEQUENCE: 8

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may or may not be present

<400> SEQUENCE: 9

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 10
<211> LENGTH: 2150
<212> TYPE: DNA
<213> ORGANISM: Homo sapiens

<400> SEQUENCE: 10
gcgtcatggc cttaccagtg accgccttgc tcctgccgct ggccttgctg ctccacgccg      60
ccaggccgag ccagttccgg gtgtcgccgc tggatcggac ctggaacctg gcgagacag     120 tggagctgaa gtgccaggtg ctgctgtcca acccgacgtc gggctgctcg tggctcttcc     180
agccgcgcgg cgccgccgcc agtcccacct tcctcctata cctctcccaa aacaagccca     240
aggcggccga ggggctggac acccagcggt tctcgggcaa gaggttgggg gacaccttcg     300 tcctcacccct gagcgacttc cgccgagaga acagggctg ctatttctgc tcggccctga     360
gcaactccat catgtacttc agccacttcg tgccggtctt cctgccagcg aagcccacca     420
cgacgccagc gccgcgacca ccaacaccgg cgcccaccat cgcgtcgcag ccctgtccc      480 tgcgcccaga ggcgtgccgg ccagcggcgg ggggcgcagt gcacacgagg gggctggact     540
tcgcctgtga tatctacatc tgggcgccct tggccggac ttgtgggt cttctcctgt        600 cactggttat caccctttac tgcaaccaca ggaaccgaag acgtgtttgc aaatgtcccc     660
ggcctgtggt caaatcggga gacaagccca gcctttcggc gagatacgtc taaccctgtg     720
caacagccac tacattactt caaactgaga tccttccttt tgagggagca agtccttccc     780

```
tttcattttt tccagtcttc ctccctgtgt attcattctc atgattatta ttttagtggg      840
ggcggggtgg gaaagattac tttttctttta tgtgtttgac gggaaacaaa actaggtaaa     900
atctacagta caccacaagg gtcacaatac tgttgtgcgc acatcgcggt agggcgtgga      960
aagggggcagg ccagagctac ccgcagagtt ctcagaatca tgctgagaga ctggaggca     1020
cccatgccat ctcaacctct tccccgcccg ttttacaaag ggggaggcta aagcccagag     1080
acagcttgat caaaggcaca cagcaagtca gggttggagc agtagctgga gggaccttgt     1140
ctcccagctc agggctcttt cctccacacc attcaggtct ttctttccga ggcccctgtc     1200
tcagggtgag gtgcttgagt ctccaacggc aagggaacaa gtacttcttg atacctggga     1260
tactgtgccc agagcctcga ggaggtaatg aattaaagaa gagaactgcc tttggcagag     1320
ttctataatg taaacaatat cagacttttt tttttataat caagcctaaa attgtataga     1380
cctaaaataa aatgaagtgg tgagcttaac cctggaaaat gaatccctct atctctaaag     1440
aaaatctctg tgaaacccct atgtggaggc ggaattgctc tcccagccct tgcattgcag     1500
aggggcccat gaaagaggac aggctacccc tttacaaata gaattgagc atcagtgagg      1560
ttaaactaag gccctcttga atctctgaat ttgagataca aacatgttcc tgggatcact     1620
gatgactttt tatactttgt aaagacaatt gttggagagc ccctcacaca gccctggcct     1680
ctgctcaact agcagataca gggatgaggc agacctgact ctcttaagga ggctgagagc     1740
ccaaactgct gtcccaaaca tgcacttcct tgcttaaggt atggtacaag caatgcctgc     1800
ccattggaga gaaaaaactt aagtagataa ggaaataaga accactcata attcttcacc     1860
ttaggaataa tctcctgtta atatggtgta cattcttcct gattattttc tacacataca     1920
tgtaaaatat gtctttcttt tttaaatagg gttgtactat gctgttatga gtggctttaa     1980
tgaataaaca tttgtagcat cctctttaat gggtaaacag catccgaaaa aaaaaaaaaa     2040
aaaaaaaaaa aaaaaaaaaa aaaaaaaaaa aaaaaaaaaa aaaaaaaaaa aaaaaaaaaa     2100
aaaaaaaaaa aaaaaaaaaa aaaaaaaaaa aaaaaaaaaa aaaaaaaaa                2150
```

<210> SEQ ID NO 11
<211> LENGTH: 235
<212> TYPE: PRT
<213> ORGANISM: Homo sapiens

<400> SEQUENCE: 11

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Cys
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
```

```
                130                 135                 140
Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 12
<211> LENGTH: 705
<212> TYPE: DNA
<213> ORGANISM: Homo sapiens

<400> SEQUENCE: 12
gcgactgtct ccgccgagcc cccggggcca ggtgtcccgg gcgcgccacg atgcggccgc     60
ggctgtggct cctcttggcc gcgcagctga cagttctcca tggcaactca gtcctccagc    120 agaccccctgc atacataaag gtgcaaacca acaagatggt gatgctgtcc tgcgaggcta    180
aaatctccct cagtaacatg cgcatctact ggctgagaca gcgccaggca ccgagcagtg    240
acagtcacca cgagttcctg gccctctggg attccgcaaa agggactatc cacggtgaag    300
aggtggaaca ggagaagata gctgtgtttc gggatgcaag ccggttcatt ctcaatctca    360
caagcgtgaa gccggaagac agtggcatct acttctgcat gatcgtcggg agccccgagc    420
tgaccttcgg gaagggaact cagctgagtg tggttgattt ccttcccacc actgcccagc    480
ccaccaagaa gtccaccctc aagaagagag tgtgccggtt acccaggcca gagacccaga    540
agggcctcaa ggggaaggtg tatcaggaac ctttgtcccc caatgcctgc atggatacta    600
cagcaatact acaacctcac agaagctgct taacccatgg atcctgaaaa cataggcaag    660
aagcacaggt cctgatgagt ggatctttac tactttttacc agatt                   705

<210> SEQ ID NO 13
<211> LENGTH: 198
<212> TYPE: PRT
<213> ORGANISM: Homo sapiens

<400> SEQUENCE: 13

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
        50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
```

```
                        100                 105                 110
Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
        130                 135                 140

Thr Lys Lys Ser Thr Leu Lys Lys Arg Val Cys Arg Leu Pro Arg Pro
145                 150                 155                 160

Glu Thr Gln Lys Gly Leu Lys Gly Lys Val Tyr Gln Glu Pro Leu Ser
                165                 170                 175

Pro Asn Ala Cys Met Asp Thr Thr Ala Ile Leu Gln Pro His Arg Ser
            180                 185                 190

Cys Leu Thr His Gly Ser
        195

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 14

Gly Asp Val Glu Xaa Asn Pro Gly Pro
1               5
```

REPROGRAMMING CD4 T CELLS INTO CYTOTOXIC CD8 CELLS BY FORCED EXPRESSION OF CD8ab AND CLASS 1 RESTRICTED T CELL RECEPTORS

CROSS-REFERENCE TO RELATED APPLICATIONS

This application is a national phase application under 35 U.S.C. § 371 that claims priority to International Application No. PCT/US2019/028202 filed Apr. 18, 2019, which claims priority to U.S. Provisional Patent Application Ser. No. 62/659,971, filed Apr. 19, 2018, both of which are incorporated by reference herein in their entirety.

REFERENCE TO SEQUENCE LISTING SUBMITTED AS A COMPLIANT ASCII TEXT FILE (.xml)

Pursuant to the EFS-Web legal framework and 37 CFR §§ 1.821-825 (see MPEP 2442.03 (a)), a Sequence Listing in the form of an ASCII-compliant text file (entitled "3000119-001001_Sequence-Listing_ST25" created on Aug. 30, 2023 and 11,311 bytes in size) is submitted with this application, and the entire contents of the Sequence Listing are incorporated herein by reference.

TECHNICAL FIELD

Embodiments of the disclosure concern at least the fields of immunology, cell biology, biology, molecular biology, cell therapy, and medicine, including at least cancer medicine.

BACKGROUND

T cell receptor (TCR) engineered adoptive T cell therapy for hematologic malignancies, such as multiple myeloma, has produced encouraging results[1]. Most TCRs targeting tumor-associated self-antigens however are isolated from autologous repertoires and have low functional avidity; the majority of T cells with high affinity TCRs are eliminated during thymic selection and surviving clones undergo peripheral fine-tuning to avoid auto-immune disease.[2,3] This modest binding affinity may limit the ability of TCR-transgenic T cells to recognize low levels of tumor associated antigens (TAA) on malignant cells. Strategies to overcome this limitation include high affinity TCR isolation from allogeneic repertoires[4] or the generation and selection of high affinity synthetic TCRs.[5,6] While such strategies can be successful,[1,5,6] they can result in severe unwanted cross-reactivity with potentially lethal off-target effects[7-9] The inventors have therefore now investigated an alternative approach. Most TCRs that target epitopes derived from TAAs are HLA-Class I restricted and under physiological conditions, the CD8αβ co-receptor increases the functional avidity of T cells expressing HLA Class I restricted TCRs.[10,11] In CD8 T cells, limited endogenous co-receptor availability may impede their full and sustained activation due to an imbalance of copy numbers between introduced TCR and endogenous CD8. T cells engineered with viral vectors express supra-physiological copy numbers of the introduced transgenes,[12] while the CD8 co-receptor is expressed at physiological levels. It is shown herein that forced expression of the CD8αβ co-receptor together with transgenic TCRs increases the overall TCR+ T cell:target cell interaction, resulting in an increased anti-tumor function.

The interplay between CD8+ and CD4+ T cells is crucial for the orchestration of an effective immune response.[13] Thus, the consequences were determined of forcing expression of the CD8αβ co-receptor in CD4+ T cells expressing transgenic HLA-Class-I-restricted TCRs. CD4+ T cells make multifaceted contributions to antigen-specific immunity to viral infections and are indispensable in the initiation and maintenance of long-term tumor control.[14] For example infusion of cytomegalovirus specific CD8+ T cell clones to treat infection after bone marrow transplantation controls viremia, but only in the presence of additional CD4+ helper T cells do these transferred CD8+ T cells persist.[15] A similar importance is imputed to CD4+ T cells when tumor-targeted T cell therapies are used. For example, neo-antigen reactive tumor infiltrating lymphocytes from a patient with metastatic cholangiocarcinoma were mostly contained in the CD4+$T_H$1 compartment, and adoptive transfer of these cells resulted in tumor regression.[16] Synergistic enhancement of anti-tumor activity of CD19 targeted chimeric antigen receptor (CAR) T cells has been reported in a Burkitt's lymphoma xenograft mouse model using CAR T cells with defined CD4:CD8 ratios,[17] while a clinical trial with a 1:1 CD4:CD8 CD19-CAR T cell ratio in the final product for lymphoma patients produced a high rate of tumor response, associated with T cell expansion and persistence of both CD4+ and CD8+ subsets,[18] indicating that both CD4+ and CD8+ tumor-specific T cells are optimal for malignant control.

The results indicate that (1) TCR+CD8+ T cell function can be enhanced with increased availability of CD8 co-receptors, and (2) CD4+ T cells with forced expression of both CD8αβ and transgenic MHC class I restricted TAA-specific TCRs are reprogrammed into multifunctional hybrid cytotoxic effector cells while preserving the helper functions of CD4+$T_H$ cells. These hybrid cells have enhanced anti-tumor function in vitro and in vivo, with reduced functional exhaustion and improved expansion, associated with increased stability of the TCR-peptide-MHC complex, and TCR signaling.

Thus, the present disclosure addresses a need in the art of adoptive transfer by providing an approach to enhance the function of co-receptor dependent TCR-transgenic CD8+ T cells and enable the use of hybrid CD4+ T cells with both cytotoxic and helper functions for adoptive transfer.

BRIEF SUMMARY

Embodiments of the disclosure include methods and compositions related to cell therapy for a mammalian individual in need thereof. The cell therapy includes cells that are engineered by the hand of man to be effective as a therapy for a medical condition, such as cancer. The cell therapy includes immune effector cells, such as T cells or NK cells that have a receptor that targets an antigen, and the receptor may be endogenous and native to the cell or may be engineered by the hand of man. In certain embodiments, the cells of the cell therapy are modified to express a protein that enhances the efficacy of the cells for the therapy, and in particular the cells also express a receptor (native to the cell or not) that targets a particular antigen. The antigen to which the receptor is targeted is a cancer antigen, in specific embodiments. Although the receptor is a T cell receptor (TCR) in at least some cases, in alternative cases the receptor is a chimeric antigen receptor (CAR), or the cell may express both.

In particular embodiments, the protein that enhances the efficacy of the cells for the therapy is cluster of differentiation 8 (CD8) comprising CD8-α and/or CD8-β chain. T cells are modified to express CD8αβ whether or not they are CD4+ T cells or CD8+ T cells. For CD8+ T cells, the increase in level of expression of CD8αβ co-receptor in the CD8+ T cells enhances the ability of native TCRs in the cells to be effective and also enhances the ability of engineered TCRs in transgenic CD8+ T cells to be effective. In cases wherein CD4+ T cells, which are naturally helper T cells, are modified to express CD8αβ, the transgenic expression allows the CD4+ T cells also to have cytotoxic activity.

Embodiments of the disclosure include methods of enhancing an immune effector cell therapy for an individual, comprising the steps of: providing to the individual an effective amount of one or both of the following: CD8+ cells that express an exogenous CD8αβ co-receptor and optionally express one or more exogenous engineered antigen receptors; and CD4+ cells that express an exogenous CD8αβ co-receptor and one or more exogenous engineered antigen receptors. In specific cases, the engineered antigen receptor is a T cell receptor (TCR), a chimeric antigen receptor (CAR) or both. The CD8+ cells, CD4+ cells, or both may be autologous or allogeneic with respect to the individual. In some cases, the exogenous engineered antigen receptor and the exogenous CD8αβ co-receptor are expressed from the same vector in the cells, and the vector may comprise one or more expression constructs that separately express the exogenous engineered antigen receptor and the exogenous CD8αβ co-receptor. In specific embodiments, the expression construct that expresses the exogenous engineered antigen receptor and the expression construct that expresses the exogenous CD8αβ co-receptor are separated by a 2A element or an IRES element. In some cases, the exogenous engineered antigen receptor and the exogenous CD8αβ co-receptor are expressed from different vectors in the cells. In any case, the vector may be a viral vector (adenoviral vector, an adeno-associated viral vector, a retroviral vector, or a lentiviral vector) or non-viral vector.

In particular embodiments of the method, the antigen is a tumor antigen or a pathogen antigen. Examples of tumor antigens include those selected from the group consisting of survivin, PRAME, CD 19, CD20, CD22, Kappa or light chain, CD30, CD33, CD 123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor cc2, IL-11 receptor R a, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-a, CD44v7/8, 8H9, NCAM, VEGF receptors, 5T4, Fetal AchR, NKG2D ligands, HER2, BCMA, CD44v6, and a combination thereof.

Methods of the disclosure may further comprise the step of providing to the individual an effective amount of the CD4+ T cells, the CD8+ T cells, or a mixture thereof. In such cases, the method may further comprise the step of providing to the individual an additional cancer therapy.

Embodiments of the disclosure include methods of producing a CD4+ T cell having cytotoxic effector cell function and helper function, comprising the step of transfecting the CD4+ T cell with an exogenous CD8αβ co-receptor and an exogenous engineered antigen receptor. The engineered antigen receptor may be a T cell receptor (TCR), a chimeric antigen receptor (CAR) or both. The exogenous engineered antigen receptor and the exogenous CD8αβ co-receptor may or may not be expressed from the same vector in the cells. In particular, the vector comprises one or more expression constructs that separately express the exogenous engineered antigen receptor and the exogenous CD8αβ co-receptor. The expression construct that expresses the exogenous engineered antigen receptor and the expression construct that expresses the exogenous CD8αβ co-receptor may be separated by a 2A element or an IRES element. Vectors include viral vectors (adenoviral vector, an adeno-associated viral vector, a retroviral vector, or a lentiviral vector) or non-viral vectors.

The antigen may be a tumor antigen or a pathogen antigen. In some cases, the tumor antigen is selected from the group consisting of survivin, PRAME, CD 19, CD20, CD22, Kappa or light chain, CD30, CD33, CD 123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor cc2, IL-11 receptor R a, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-a, CD44v7/8, 8H9, NCAM, VEGF receptors, 5T4, Fetal AchR, NKG2D ligands, HER2, BCMA, CD44v6, and a combination thereof.

Methods of the disclosure may further comprise the step of providing to the individual an effective amount of the CD4+ T cells to an individual in need thereof, such as one who has cancer. An effective amount of CD8+ T cells expressing an exogenous CD8αβ co-receptor, an exogenous engineered antigen receptor, or both may be provided to the individual, the individual may also be receiving an additional cancer therapy.

Embodiments of the disclosure include methods of enhancing cytotoxicity of CD8+ T cells, comprising the step of transfecting the CD8+ T cell with an exogenous CD8αβ co-receptor. The CD8+ T cells may also express an exogenous engineered antigen receptor, such as a T cell receptor (TCR), a chimeric antigen receptor (CAR) or both. The exogenous engineered antigen receptor and the exogenous CD8αβ co-receptor are expressed from the same vector in the cells. The vector may comprise one or more expression constructs that separately express the exogenous engineered antigen receptor and the exogenous CD8αβ co-receptor. In some cases, the expression construct that expresses the exogenous engineered antigen receptor and the expression construct that expresses the exogenous CD8αβ co-receptor are separated by a 2A element or an IRES element. The exogenous engineered antigen receptor and the exogenous CD8αβ co-receptor may be expressed from different vectors in the cells. Viral vectors (adenoviral vector, an adeno-associated viral vector, a retroviral vector, or a lentiviral vector) or non-viral vectors may be utilized.

Antigens include tumor antigens or pathogen antigens. Tumor antigens include those selected from the group consisting of CD 19, CD20, CD22, Kappa or light chain, CD30, CD33, CD 123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor cc2, IL-11 receptor R a, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-a, CD44v7/8, 8H9, NCAM, VEGF receptors, 5T4, Fetal AchR, NKG2D ligands, HER2, BCMA, CD44v6, and a combination thereof. The method may further comprise the step of providing to the individual an effective amount of the CD8+ T cells to an individual in need thereof. The method may further comprise the step of providing to the individual an effective amount of CD4+ T cells to an individual in need thereof. The CD4+ T cells may be engineered to express an exogenous CD8αβ co-receptor, an exogenous engineered antigen receptor, or both. The individual may have cancer, and the method may further comprise the step of providing to the individual an additional cancer therapy.

Embodiments of the disclosure concern compositions comprising CD4+ T cells transgenically expressing CD8αβ co-receptor. The CD4+ T cells may also transgenically express one or more exogenous engineered antigen receptors, such as a TCR, a CAR, or both. The composition may further comprise CD8+ T cells of any kind, including CD8+ T cells that transgenically express CD8αβ co-receptor, one or more exogenous engineered antigen receptors, or both.

Embodiments of the disclosure include compositions comprising CD8+ T cells transgenically expressing CD8αβ co-receptor and optionally one or more exogenous engineered antigen receptors. The engineered antigen receptor may be a TCR, a CAR, or both. The composition may further comprise CD4+ T cells of any kind, including CD4+ T cells that transgenically express CD8αβ co-receptor, one or more exogenous engineered antigen receptors, or both.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure. Additional objects, features, aspects and advantages of the present invention will be set forth in part in the description which follows, and in part will be obvious from the description or may be learned by practice of the invention. Various embodiments of the disclosure will be described in sufficient detail to enable those skilled in the art to practice the invention, and it is to be understood that other embodiments may be utilized and that changes may be made without departing from the scope of the invention. The following detailed description is, therefore, not be taken in a limiting sense, and the scope of the present invention is best defined by the appended claims.

BRIEF DESCRIPTION OF THE DRAWINGS

For a more complete understanding of the present disclosure, reference is now made to the following descriptions taken in conjunction with the accompanying drawing, in which:

FIGS. 1A-1E: CD4+ T cells convert to a hybrid phenotype upon transduction with a class I TCR and CD8αβ. (FIG. 1A) Schemes of retroviral vectors. (FIG. 1B) Transduction efficiency of CD4+(red squares) or CD8+(black circles) T cells with TCR or T8 vectors compared to NT controls, n=6. Representative histograms of CD8α expression (FIG. 1C), CD8β expression (FIG. 1D) and survivin LML dextramer staining (FIG. 1E) in CD4+ and CD8+ T cells (upper panels), and MFI summaries (lower panels), n=5-7 donors. (FIGS. 1C, 1D, 1E) NT: gray, TCR+: blue, T8+: green lines. Mean±SD, NS: not significant, $*p \leq 0.05$, $p \leq 0.01$, $*p \leq 0.001$, $****p \leq 0.0001$.

FIGS. 3A-3F. Co-expression of CD8αβ with TCR confers sequential killing ability to CD4+ T cells and improves CD8+ T cell function. (FIG. 3A) Co-culture of NT, TCR+ or T8+CD4+(red bars) or CD8+(black bars) T cells with BV173 leukemia cells (HLA-A2*02:01+survivin+); E:T ratio 1:5, residual BV173 cells quantified on day 3, n=7. (FIG. 3B) Co-culture of NT, TCR+ or T8+CD4+(left) or CD8+(right) T cells with wild type (WT) BV173 (solid bars) or β2-microglobulin knock out (B2M-KO) BV173 cells (open bars); E:T ratio 1:5, residual BV173 cells quantified on day 3, n=3. (FIG. 3C) Experimental setup of sequential co-cultures. (FIG. 3D) Sequential co-cultures of CD4+(left) or CD8+(right) T cells. Quantification of tumor (top panels) and T cells (lower panels) over time, with tumor cell re-challenge (+), n=7. T cell expansion: TCR+vs T8+CD4: p<0.0001; TCR+vs T8+CD8: p=NS; T8+CD4 vs TCR+CD8: p=0.002; T8+CD4 vs CD8, p=0.015, t-test on log AUC. (FIG. 3E) Cytokine quantification in co-culture supernatants 24 hours after first tumor challenge (D1) and 24 hours after third tumor challenge (D10), n=6. (FIG. 3F) Fold T cell expansion of NT, TCR+ or T8+CD4+(red) and CD8+ (black) T cells from HLA-A*02+(top panels) or HLA-A*02-(bottom panels) donors, n=3-4. (FIGS. 3A, 3B, 3E, 3F) Mean±SD, NS: not significant, $*p \leq 0.05$, $p \leq 0.01$, $*p \leq 0.001$, $****p \leq 0.0001$.

(FIG. 4A) Single-cell quantification of the kinetics of interaction between T cells and target cells by TIMING. $t_{Seek}$: time to first encounter of effector and target cell, $t_{Contact}$: time of conjugation between effector and target cell, $t_{Death}$: time from first contact to target cell apoptosis. (FIG. 4B) Cumulative incidence of a single effector cell in finding ($t_{Seek}$) one (left, E:T 1:1) or two (right, E:T 1:2) target cells (top row), in forming a stable synapse with the target ($t_{Contact}$, middle row) or in killing the target ($t_{Death}$). TCR+ CD4+ T cells (red dotted lines), T8+CD4+ T cells (red solid lines), TCR+CD8+ T cells (black dotted lines) and T8+CD8+ T cells (black solid lines). NS: not significant, $*p \leq 0.05$, $p \leq 0.01$, $*p \leq 0.001$, $****p \leq 0.0001$, log-rank test.

(FIG. 5A) Representative FACS histograms of pLck Y394 phosphorylation NT (gray), TCR+(blue) and T8+(green) CD4+ or CD8+ T cells. (FIG. 5B) Summary of pLCK MFI normalized to MFI in NT control cells. n=4 donors, mean±SD, CD4 TCR+vs T8+: 104±11 vs 173±35%, CD8 TCR+vs T8+: 106±7 vs 126±13%, T8+CD8 vs CD4: 126±13 vs 173±35%. NS: not significant, *p≤0.05, p≤0.01, *p≤0.001, ****p≤0.0001.

(FIG. 6A) Experimental set up. (FIGS. 6B, 6D) Summary of BLI data from mice treated with (FIG. 6B) CD8+ T cells or (FIG. 6D) CD4+ T cells. Non-transduced (NT) control T cells (n=5, gray), TCR+ T cells (n=5, blue), 18+ T cells (n=5, green). (FIG. 6B) CD8: NT vs TCR+: p=0.0002, NT vs T8+: p<0.0001, TCR+vs T8+: p=0.01, t-test on log AUC on day 28 compared to day 0. (FIG. 6D) CD4: TCR+vs T8+: p=0.001, t-test on log AUC on day 35 compared to day 0. (FIGS. 6C, 6E) 3 representative mice/group imaged over time by BLI, color scale $5\times10^3$ to $5\times10^4$ $p/sec/cm^2/sr$ for (FIG. 6C) CD8+ T cells and (FIG. 6E) CD4+ T cells.

DETAILED DESCRIPTION

I. Examples of Definitions

Figure 1C:
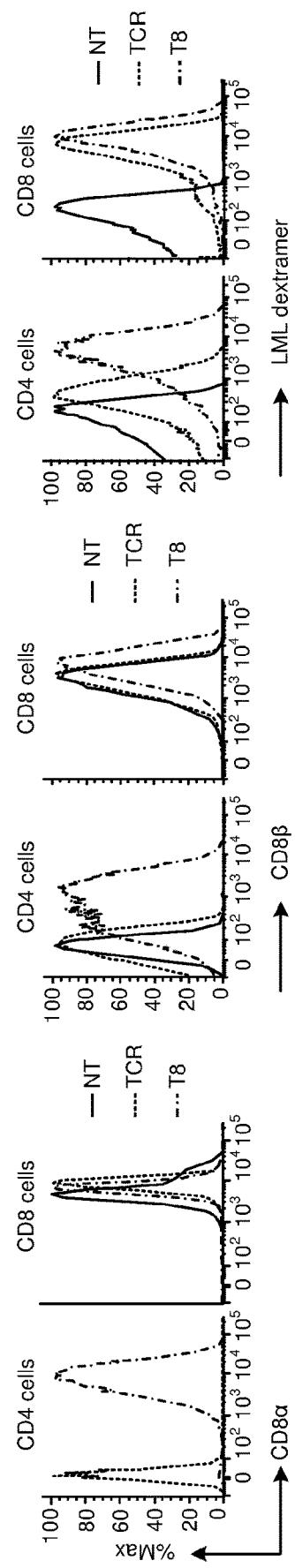

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein embodiments which are disclosed and still obtain a like or similar result without departing from the spirit and scope of the disclosure. The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this application, the term "about" is used according to its plain and ordinary meaning in the area of cell and molecular biology to indicate that a value includes the standard deviation of error for the device or method being employed to determine the value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "engineered antigen receptor" as used herein refers to a synthetic cell surface protein that binds to a specific antigen and that has been generated by the hand of man.

The term "exogenous" as used herein with respect to a cell, for example, refers to a molecule that is provided to the cell by recombinant engineering methods from the hand of man. The term differentiates from endogenous molecules that are native to the cell found in nature.

"Treating" or treatment of a disease or condition refers to executing a protocol, which may include administering one or more drugs or therapies (including cells) to a patient, in an effort to alleviate at least one sign or symptom of the disease. Desirable effects of treatment include decreasing the rate of disease progression, ameliorating or palliating the disease state, delaying the onset of at least one symptom, and remission or improved prognosis. Alleviation can occur prior to signs or symptoms of the disease or condition appearing, as well as after their appearance, or both. Thus, "treating" or "treatment" may include "preventing" or "prevention" of disease or undesirable condition. In addition, "treating" or "treatment" does not require complete alleviation of one or more signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of the condition. This includes, but is not limited to, a reduction in the frequency or severity of one or more signs or symptoms of a disease. For example, treatment of cancer may involve, for example, a reduction in the size of a tumor, a reduction in the invasiveness of a tumor, reduction in the growth rate of the cancer, and/or prevention of metastasis. Treatment of cancer may also refer to prolonging survival of a subject with cancer.

"Subject" and "patient" and "individual" refer to either a human or non-human, such as primates, mammals, and vertebrates. In particular embodiments, the subject is a human, dog, cat, horse, cow, and so forth.

The phrases "pharmaceutically acceptable or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

II. General Embodiments

Embodiments of the disclosure include improvements upon receptor-engineered adoptive T cell therapy. Methods of the disclosure expand upon effective options for adoptive T cell therapy by modifying the cells of the therapy to be able to target low avidity antigens with engineered receptors without having to utilize high affinity receptors that can result in deleterious effects with their use.

A. CD4+ T Cells

Methods of the disclosure include the production of CD4+ T cells having both helper functions and cytotoxicity for adoptive transfer upon transgenic expression of CD8αβ chains. In specific cases, there are methods of producing CD4+ T cells having surface expression of CD8αβ chains for the purpose of producing CD4+ T cells comprising the capacity to recognize and bind targeted pMHC Class I complexes.

CD4+ T cells of the disclosure are produced herein having the activity of recognizing class I epitopes. Thus, the methods encompassed herein re-direct CD4+ cells to a Class I restricted epitope as a result of transgenically expressing CD8αβ. In addition to the cells being able to recognize class I epitopes, the cells also have the activity of expressing $T_H1$ cytokines, such as IFNγ, TNFα, perforin, and/or granzyme B, in addition to their natural activity of expressing $T_H2$.

Embodiments of the disclosure include methods and compositions in which CD4+ T cells (and CD8+ T cells) comprise CD8αβ transgenic expression that renders the cells to lack significant fratricide activity, including as compared to T cells in expansion without transgenic expression of CD8αβ.

In particular embodiments, transgenic CD4+ T cells expressing sufficient levels of CD8αβ become class I pMHC-targeted hybrid cytotoxic and helper T cells that effectively have both CD8+ and CD4+ T cell functions at the single cell level. As such, CD8αβ reprograms single CD4+ T cells with low-avidity class I TCRs into hybrid cytotoxic and helper T cells with enhanced in vivo function.

Embodiments of the disclosure include the reprogramming of CD4+ T cells to have activities of CD4+ and CD8+ T cells. In specific embodiments, CD4+ T cells comprise helper T cell activity in addition to cytotoxicity activity. Thus, in specific cases CD4+ T cells are both hybrid and multifunctional. In specific cases, the CD4+ T cells are engineered to have these characteristics by expressing transgenic, exogenously provided CD8 co-receptor, and such cells are able to produce both $T_H1$ and $T_H2$ cytokines. The cells also comprise serial killer activity and comprise anti-tumor function.

The ability of the CD8 co-receptor-expressing CD4+ cells to comprise cytotoxicity may be utilized with respect to one or more exogenous engineered antigen receptors, including TCRs and CARs.

B. CD8+ T Cells

In specific embodiments, methods and compositions concern utilization of an exogenous CD8αβ co-receptor in CD8+ T cells to increase the effectiveness of the cells. In specific cases the CD8+ T cells express an exogenous engineered antigen receptor (such as HLA Class I-restricted TCRs) and the co-expression of CD8αβ co-receptor in the cells improves the functional avidity of the cells. In other cases, CD8+ T cells are modified to express an exogenous CD8αβ co-receptor that enhances the activity of endogenous TCRs.

The methods and compositions allow for advancements in CD8+ T cell therapy at least by increasing the availability of CD8 αβ co-receptors in the CD8+ T cells, including increasing the cell-surface levels of CD8αβ over levels naturally present in the cells. Therefore, in utilizing CD8+ T cells for a cell therapy of any kind, in specific embodiments the CD8+ T cells express exogenous CD8αβ co-receptors.

Embodiments include enhancing the function of a population of CD8+ T cells by increasing the availability of CD8 co-receptors in at least some of the cells in the population. Methods of the disclosure overcome the limiting factor of there being too few endogenous CD8 co-receptors in CD8+ T cells for adoptive transfer applications, for example. Thus, in particular embodiments of the disclosure, there are methods of increasing the availability of CD8 co-receptors in CD8+ T cells to enhance the function of the CD8+ T cells.

The CD8 co-receptors may be utilized in CD8+ T cells whether or not the cells are transgenic for an artificial antigen receptor. In specific embodiments, the methods and compositions of the disclosure enhance the function of receptor-transgenic (TCR and/or CAR, for example) CD8+ T cells.

C. CD4+ and CD8+ T Cells

Embodiments of the disclosure encompass improvements upon adoptive transfer using T cells for an individual. The known methods of utilizing CD8+ T cells as cytotoxic T cells for adoptive transfer have now been improved upon by also allowing utilization of CD4+ T cells that have non-natural cytotoxic activity. Embodiments of the disclosure encompass harnessing CD8 co-receptor function for immunotherapy with TCR transgenic T cells, including low-avidity TCR transgenic T cells that are CD4+ or CD8+, or a functional hybrid thereof.

Embodiments of the disclosure provide for the enhancement of CD8 T cell function for natural and/or exogenously provided TCRs or other antigen receptors in the CD8 cells. The enhancement may include advantages such as increasing their serial tumor killing capacity compared to such T cells that respectively lack expression of exogenously provided CD8αβ.

In particular embodiments, a mixture of CD4+ T cells expressing sufficient levels of CD8αβ co-receptor and an exogenous engineered antigen receptor and of CD8+ expressing sufficient levels of CD8αβ co-receptor and optionally an exogenous engineered antigen receptor are utilized in certain methods. The mixture may utilize a specific ratio of CD4+ T cells to CD8+ T cells, such as 10:1, 5:1, 2:1, 1:1, 1:2, 1:5, 1:10, 1:25, 1:50, 1:100, 1:500, 1:1000, 1:10,000, and so on.

The examples provided elsewhere herein address the need for effective and safe TCR-expressing cells. Most naturally occurring class I restricted TCRs that target overexpressed tumor-associated self-antigens (TAAs) are of low avidity because of selection and tolerance in the host and are CD8 co-receptor dependent. Adoptive T cell transfers with TCR-engineered T cells thus completely rely on the function of CD8+ T cells and cannot exploit beneficial CD4+ T cell functions. Hence, the present disclosure concerns a novel strategy that combines expression of a TAA-specific low-avidity TCR with the CD8αβ co-receptor and the properties of purified transgenic CD8+ and CD4+ T cells separately were characterized. It was determined that CD8c43 co-transfer enhanced TCR+CD8+ T cell function by increasing their serial tumor killing capacity, indicating that limited availability of endogenous CD8 co-receptors impedes full deployment of their functional potential. Engineered CD4+ T cells were efficiently reprogrammed into hybrid multifunctional cytotoxic and helper T cells at the single cell level: they recognized and killed cells expressing the cognate class I restricted tumor antigen, became serial killers, produced mostly $T_H1$ and preserved some $T_H2$ cytokines, and showed superior anti-tumor function in vivo. Thus, embodiments of the disclosure concern at least (1) enhancement of the function of TCR-transgenic CD8+ T cells and (2) manufacture of class I pMHC targeted hybrid cytotoxic and helper T cells with both CD8+ and CD4+ T cell functions readily available at the single cell level.

III. Examples of Compositions

The present disclosure concerns CD4+ T cells and CD8+ T cells for use in adoptive transfer. The CD4+ T cells and CD8+ T cells of the present disclosure are not found in nature at least because they separately express at least one exogenously provided protein: CD8αβ co-receptor. In particular cases both the α and β chains of CD8 are expressed in the same cell. The CD8αβ co-receptor may or may not be transiently expressed in the cells. The CD8+ cells transgenically expressing CD8αβ co-receptor are not the CD8+ cells in nature having natural expression of CD8αβ co-receptor at least because the level of CD8αβ co-receptor molecules is greater than cells that naturally express it in nature, and this difference in expression level leads to a functional difference of the transgenic CD8+ T cells having greater efficacy than native CD8+ T cells.

In particular embodiments, the CD4+ T cells and CD8+ T cells in addition to expressing CD8αβ co-receptor also express one or more engineered antigen receptors. The one or more engineered antigen receptors may be of any kind, but in specific cases they are HLA-Class-I restricted TCRs or chimeric antigen receptors (CARs).

A. T Cell Receptor (TCR)

In some embodiments, the engineered antigen receptors include recombinant TCRs and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail. For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MEC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains comprise a constant domain. For example, like immunoglobulins, the extracellular portion of TCR chains (e.g., α-chain, β-chain) can contain two immunoglobulin domains, a variable domain (e.g., $V_a$ or Vβ; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., α-chain constant domain or $C_a$, typically amino acids 117 to 259 based on Kabat, β-chain constant domain or Cβ, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains may comprise a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). In some embodiments, phage display is used to isolate TCRs against a target antigen. In some embodiments, the TCR or antigen-binding portion thereof can be synthetically generated from knowledge of the sequence of the TCR.

B. Chimeric Antigen Receptors

In some embodiments, the engineered antigen receptors include CARs, including activating or stimulatory CARs, costimulatory CARs (see WO2014/055668), and/or inhibitory CARs. The CARs generally include an extracellular antigen (or ligand) binding domain linked to one or more intracellular signaling components, in some aspects via linker(s) and/or transmembrane domain(s). Such molecules typically mimic or approximate a signal through a natural antigen receptor, a signal through such a receptor in combination with a costimulatory receptor, and/or a signal through a costimulatory receptor alone. The CAR may be first generation, second generation, or third or subsequent generation.

In some embodiments, the CAR is encoded by a vector and comprises at least: a) an intracellular signaling domain, b) a transmembrane domain, and c) an extracellular domain comprising at least one antigen binding region.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain having one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be derived from human genes used to enhance cellular immunotherapy for human patients. In a specific embodiment, the disclosure includes a full-length CAR cDNA or coding region encoded by the vector. The antigen binding regions or domain may comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion may or may not be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and one or more intracellular signaling domains, such as a CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3 □, an additional signal provided by a human costimulatory receptor inserted in a human CAR may be utilized for full activation of NK cells and could help improve in vivo persistence and the therapeutic success of the adoptive immunotherapy.

In some embodiments, a CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In certain embodiments of the CAR, the antigen-specific portion of the receptor (which may be referred to as an extracellular domain comprising an antigen binding region) comprises a tumor associated antigen binding domain or a pathogen-specific antigen binding domain. Antigens include carbohydrate antigens recognized by pattern-recognition receptors. A tumor associated antigen may be of any kind so long as it is expressed on the cell surface of tumor cells.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in an expression vector in proper orientation for expression. The polycistronic modular vector of the disclosure may be a viral vector or may not be a viral vector, such as a plasmid. Although for illustrative embodiments the vector detailed herein is a retroviral vector, in other cases the vector is also a viral vector but is instead an adenoviral vector, adeno-associated viral vector, or lentiviral vector, for example.

Any vector can be used to introduce the chimeric construct into immune cells. Suitable vectors for use in accordance with the method of the present disclosure may be non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV. In specific cases, the vector is based on the Moloney Murine Leukemia Virus.

In some aspects, the antigen-specific binding or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source.

Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as T, NK, iNKT, B, or MSC cells, comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand CAR$^+$ immune cells.

A single vector may encode two separate CAR molecules, or a single vector may encode one or more CAR molecules at least one of which has specificity for two non-identical antigens, such as a bispecific CAR, a bispecific TCR, or a bispecific CAR/TCR. The antigen receptors encoded by the vectors of the disclosure, the vectors themselves, and cells harboring the vector are generated by the hand of man and are not present in nature.

In some embodiments, the CAR comprises an extracellular antigen-recognition domain that specifically binds to an antigen. The CAR may be specifically designed to target an antigen of a particular tissue or cell type. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MEC) molecule.

C. Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including solid tumors, hematologic cancers, cancers of the immune system, such as lymphomas, leukemias, and/or myelomas, such as B, T, and myeloid leukemias, lymphomas, and multiple myelomas as well as autoimmune or alloimmune conditions. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells. In some cases, the antigen is associated with an immune-related disorder. In cases wherein the disease is a pathogenic disease, the antigen will be a tumor of the pathogen, such as a virus, fungus, protozoa, or bacteria.

Any suitable antigen may find use in the present method. Exemplary antigens include, but are not limited to, antigenic molecules from infectious agents, auto-/self-antigens, tumor-/cancer-associated antigens, and tumor neoantigens (Linnemann et al., 2015). In particular aspects, the antigens include survivin, PRAME, NY-ESO, EGFRvIII, Muc-1, Her2, CA-125, WT-1, Mage-A3, Mage-A4, Mage-A10, TRAIL/DR4, and CEA. In particular aspects, the antigens for the two or more antigen receptors include, but are not limited to, CD19, EBNA, WT1, CD123, NY-ESO, EGFRvIII, MUC1, HER2, CA-125, WT1, Mage-A3, Mage-A4, Mage-A10, TRAIL/DR4, and/or CEA. The sequences for these antigens are known in the art, for example, CD19 (Accession No. NG_007275.1), EBNA (Accession No. NG_002392.2), WT1 (Accession No. NG_009272.1), CD123 (Accession No. NC_000023.11), NY-ESO (Accession No. NC_000023.11), EGFRvIII (Accession No. NG_007726.3), MUC1 (Accession No. NG_029383.1), HER2 (Accession No. NG_007503.1), CA-125 (Accession No. NG_055257.1), WT1 (Accession No. NG_009272.1), Mage-A3 (Accession No. NG_013244.1), Mage-A4 (Accession No. NG_013245.1), Mage-A10 (Accession No. NC_000023.11), TRAIL/DR4 (Accession No. NC_000003.12), and/or CEA (Accession No. NC_000019.10).

Tumor-associated antigens may be derived from prostate, breast, colorectal, lung, pancreatic, renal, mesothelioma, ovarian, or melanoma cancers, or hematologic malignancies. Exemplary tumor-associated antigens or tumor cell-derived antigens include MAGE 1, 3, and MAGE 4 (or other MAGE antigens such as those disclosed in International Patent Publication No. WO99/40188); PRAME; survivin, BAGE; RAGE, Lage (also known as NY ESO 1); SAGE; and HAGE or GAGE. These non-limiting examples of tumor antigens are expressed in a wide range of tumor types such as melanoma, lung carcinoma, sarcoma, and bladder carcinoma, or hematologic malignancies. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP).

Other tumor associated antigens include Plu-1, HASH-1, HasH-2, Cripto and Criptin. Additionally, a tumor antigen may be a self peptide hormone, such as whole length gonadotrophin hormone releasing hormone (GnRH), a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WTI), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDc127/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STATS, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), polyomavirus (e.g., BK virus and JC virus), adenovirus, Staphylococcus species including Methicillin-resistant Staphylococcus aureus (MRSA), and Streptococcus species including Streptococcus pneumoniae. As would be understood by the skilled person, proteins derived from these and other pathogenic microorganisms for use as antigen as described herein and nucleotide sequences encoding the proteins may be identified in publications and in public databases such as GENBANK®, SWISS-PROT®, and TREMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein. Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and 1E2 (UL123 and UL122), protein products from the cluster of genes from UL128-UL150 (Rykman, et al., 2006), envelope glycoprotein B (gB), gH, gN, and pp150. As would be understood by the skilled person, CMV proteins for use as antigens described herein may be identified in public databases such as GENBANK®, SWISS-PROT®, and TREMBL® (see e.g., Bennekov et al., 2004; Loewendorf et al., 2010; Marschall et al., 2009).

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B (see, e.g., Lockey et al., 2008).

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M) (see, e.g., Rieder et al., 1999).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2.

Exemplary viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be a bacterial antigen. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., 2007). As would be understood by the skilled person, *Staphylococcus* proteins for use as antigens may also be identified in other public databases such as GenBank®, Swiss-Prot®, and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC).

Antigenic proteins of *Streptococcus pneumoniae* are also known in the art and may be used as an antigen in some embodiments (see, e.g., Zysk et al., 2000). The complete genome sequence of a virulent strain of *Streptococcus pneumoniae* has been sequenced and, as would be understood by the skilled person, *S. pneumoniae* proteins for use herein may also be identified in other public databases such as GENBANK®, SWISS-PROT®, and TREMBL®. Proteins of particular interest for antigens according to the present disclosure include virulence factors and proteins predicted to be exposed at the surface of the pneumococci (see, e.g., Frolet et al., 2010).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y. pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phia-* lemonium polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

D. CD8αβ Co-Receptor

In specific embodiments, the CD4+ and CD8+ cells of the disclosure express exogenous CD8αβ co-receptor. The CD8αβ co-receptor is from a mammalian source, in specific embodiments and may be human, rat, mouse, and so forth.

One example of a CD8α nucleic acid molecule is in the NCBI GenBank® Database at Accession No. BC025715 (SEQ ID NO: 10), the sequence of which is provided below:

```
   1 gcgtcatggc cttaccagtg accgccttgc
     tcctgccgct ggccttgctg ctccacgccg
  61 ccaggccgag ccagttccgg gtgtcgccgc
     tggatcggac ctggaacctg ggcgagacag
 121 tggagctgaa gtgccaggtg ctgctgtcca
     acccgacgtc gggctgctcg tggctcttcc
 181 agccgcgcgg cgccgccgcc agtcccacct
     tcctcctata cctctcccaa aacaagccca
 241 aggcggccga ggggctggac acccagcggt
     tctcgggcaa gaggttgggg gacaccttcg
 301 tcctcaccct gagcgacttc cgccgagaga
     acgagggctg ctatttctgc tcggccctga
 361 gcaactccat catgtacttc agccacttcg
     tgccggtctt cctgccagcg aagcccacca
 421 cgacgccagc gccgcgacca ccaacaccgg
     cgcccaccat cgcgtcgcag cccctgtccc
 481 tgcgcccaga ggcgtgccgg ccagcggcgg
     ggggcgcagt gcacacgagg gggctggact
 541 tcgcctgtga tatctacatc tgggcgccct
     tggccgggac ttgtgggggtc cttctcctgt
 601 cactggttat cacccttac tgcaaccaca
     ggaaccgaag acgtgtttgc aaatgtcccc
 661 ggcctgtggt caaatcggga gacaagccca
     gcctttcggc gagatacgtc taaccctgtg
 721 caacagccac tacattactt caaactgaga
     tccttccttt tgagggagca agtccttccc
 781 tttcattttt tccagtcttc ctccctgtgt
     attcattctc atgattatta ttttagtggg
 841 ggcggggtgg gaaagattac tttttcttta
     tgtgtttgac gggaaacaaa actaggtaaa
 901 atctacagta caccacaagg gtcacaatac
     tgttgtgcgc acatcgcggt agggcgtgga
 961 aaggggcagg ccagagctac ccgcagagtt
     ctcagaatca tgctgagaga gctggaggca
1021 cccatgccat ctcaacctct tccccgcccg
     ttttacaaag ggggaggcta aagcccagag
1081 acagcttgat caaaggcaca cagcaagtca
     gggttggagc agtagctgga gggaccttgt
```

```
1141 ctcccagctc agggctcttt cctccacacc
     attcaggtct ttctttccga ggcccctgtc
1201 tcagggtgag gtgcttgagt ctccaacggc
     aagggaacaa gtacttcttg atacctggga
1261 tactgtgccc agagcctcga ggaggtaatg
     aattaaagaa gagaactgcc tttggcagag
1321 ttctataatg taaacaatat cagactttt
     tttttataat caagcctaaa attgtataga
1381 cctaaaataa aatgaagtgg tgagcttaac
     cctggaaaat gaatccctct atctctaaag
1441 aaaatctctg tgaaacccct atgtggaggc
     ggaattgctc tcccagccct tgcattgcag
1501 aggggcccat gaaagaggac aggctacccc
     tttacaaata gaatttgagc atcagtgagg
1561 ttaaactaag gccctcttga atctctgaat
     ttgagataca aacatgttcc tgggatcact
1621 gatgactttt tatactttgt aaagacaatt
     gttggagagc ccctcacaca gccctggcct
1681 ctgctcaact agcagataca gggatgaggc
     agacctgact ctcttaagga ggctgagagc
1741 ccaaactgct gtcccaaaca tgcacttcct
     tgcttaaggt atggtacaag caatgcctgc
1801 ccattggaga gaaaaaactt aagtagataa
     ggaaataaga accactcata attcttcacc
1861 ttaggaataa tctcctgtta atatggtgta
     cattcttcct gattattttc tacacataca
1921 tgtaaaatat gtctttcttt tttaaatagg
     gttgtactat gctgttatga gtggctttaa
1981 tgaataaaca tttgtagcat cctcttaat
     gggtaaacag catccgaaaa aaaaaaaaa
2041 aaaaaaaaaa aaaaaaaaaa aaaaaaaaaa
     aaaaaaaaaa aaaaaaaaaa aaaaaaaaaa
2101 aaaaaaaaaa aaaaaaaaaa aaaaaaaaaa
```

One example of a CD8α protein molecule is in the NCBI GenBank® Database at Accession No. AAH25715 (SEQ ID NO: 11), the sequence of which is provided below:

```
  1 malpvtalll plalllhaar psqfrvspld
    rtwnlgetve lkcqvllsnp tsgcswlfqp
 61 rgaaasptfl lylsqnkpka aegldtqrfs
    gkrigdtfvl tlsdfrrene gcyfcsalsn
```

```
121 simyfshfvp vflpakpttt paprpptpap
    tiasqplslr peacrpaagg avhtrgldfa
181 cdiyiwapla gtcgvlllsl vitlycnhrn
    rrrvckcprp vvksgdkpsl saryv
```

One example of a CD8β nucleic acid molecule is in the NCBI GenBank® Database at Accession No. BC100912 (SEQ ID NO: 12), the sequence of which is provided below:

```
  1 gcgactgtct ccgccgagcc cccggggcca
    ggtgtcccgg gcgcgccacg atgcggccgc
 61 ggctgtggct cctcttggcc gcgcagctga
    cagttctcca tggcaactca gtcctccagc
121 agacccctgc atacataaag gtgcaaacca
    acaagatggt gatgctgtcc tgcgaggcta
181 aaatctccct cagtaacatg cgcatctact
    ggctgagaca gcgccaggca ccgagcagtg
241 acagtcacca cgagttcctg gccctctggg
    attccgcaaa agggactatc cacggtgaag
301 aggtggaaca ggagaagata gctgtgtttc
    gggatgcaag ccggttcatt ctcaatctca
361 caagcgtgaa gccggaagac agtggcatct
    acttctgcat gatcgtcggg agccccgagc
421 tgacccttcgg gaagggaact cagctgagtg
    tggttgattt ccttcccacc actgcccagc
481 ccaccaagaa gtccacccctc aagaagagag
    tgtgccggtt acccaggcca gagacccaga
541 agggcctcaa ggggaaggtg tatcaggaac
    ctttgtcccc caatgcctgc atggatacta
601 cagcaatact acaacctcac agaagctgct
    taacccatgg atcctgaaaa cataggcaag
661 aagcacaggt cctgatgagt ggatctttac
```

One example of a CD8β protein molecule is in the NCBI GenBank® Database at Accession No. AAI00913 (SEQ ID NO: 13), the sequence of which is provided below:

```
  1 mrprlwllla aqltvlhgns vlqqtpayik
    vqtnkmvmls ceakislsnm riywlrqrqa
 61 pssdshhefl alwdsakgti hgeeveqeki
    avfrdasrfi lnltsvkped sgiyfcmivg
121 speltfgkgt qlsvvdflpt taqptkkstl
    kkrvcrlprp etqkglkgkv yqeplspnac
181 mdttailqph rsclthgs
```

E. Cells for Production

CD4+ and CD8+ cells may be selected from samples from one or more individuals. The samples may be from an individual being treated and therefore are autologous with respect to the individual being treated. In other cases, the samples are from an individual other than the individual being treated with the cells and therefore are allogeneic with respect to the individual being treated. The CD4+ and CD8+ cells may be selected from immune cells isolated from subjects, particularly human subjects, including individuals in need of a therapy. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells from which the CD4+ and CD8+ cells are derived can be obtained from a subject in need of therapy or suffering from a disease. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells may or may not be human-leukocyte-antigen (HLA)-compatible. To be rendered subject-compatible, allogeneic cells can be treated to reduce immunogenicity (Fast et al., 2004).

F. Methods of Production

One of skill in the art would be well-equipped to construct a vector through standard recombinant techniques (see, for example, Sambrook et al., 2001 and Ausubel et al., 1996, both incorporated herein by reference) for the expression of the transgenic molecules of the present disclosure. The transgenic molecules may be provided to a recipient cell in or on a vector, including a viral vector or a non-viral vector. Examples of viral vectors include adenoviral, adeno-associated viral, lentiviral, or retroviral. Examples of non-viral vectors include plasmids, liposomes, nanoparticles, and the like. In specific embodiments the vector is retroviral.

1. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells may be comprised of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters, for example. In cases wherein the vector is utilized for the generation of cancer therapy, a promoter may be effective under conditions of hypoxia.

a. Promoter/Enhancers

The expression constructs provided herein comprise a promoter to drive expression of the antigen receptor and other cistron gene products. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, for example, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp-) promoter systems. In addition to producing nucleic acid sequences of promoters and enhancers synthetically, sequences may be produced using recombinant cloning and/or nucleic acid amplification technology, including PCR™, in connection with the compositions disclosed herein. Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter, GADPH promoter, metallothionein promoter; and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at GenBank®, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present disclosure.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

b. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Certain 2A sequence elements may be used to generate linked- or co-expression of genes in the constructs provided in the present disclosure. For example, cleavage sequences could be used to co-express genes by linking open reading frames to form a single cistron. An exemplary cleavage sequence is the equine rhinitis A virus (E2A) or the F2A (Foot-and-mouth disease virus 2A) or a "2A-like" sequence (e.g., *Thosea asigna* virus 2A; T2A) or porcine teschovirus-1 (P2A). In specific embodiments, in a single vector the multiple 2A sequences are non-identical, although in alternative embodiments the same vector utilizes two or more of the same 2A sequences. Examples of 2A sequences are provided in US 2011/0065779 which is incorporated by reference herein in its entirety.

In embodiments wherein self cleaving 2A peptides are utilized, the 2A peptides may be 18-22 amino-acid (aa)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (*thosea asigna* virus 2A) were also identified. The mechanism of 2A-mediated "self-cleavage" was discovered to be ribosome skipping the formation of a glycyl-prolyl peptide bond at the C-terminus of the 2A. A highly conserved sequence GDVEXNPGP (SEQ ID NO: 14) is shared by different 2As at the C-terminus, and is useful for the creation of steric hindrance and ribosome skipping. Successful skipping and recommencement of translation results in two "cleaved" proteins. Examples of 2A sequences are as follows:

T2A:

(SEQ ID NO: 6)
(GSG) E G R G S L L T C G D V E E N P G P

-continued

P2A:
(SEQ ID NO: 7)
(GSG) A T N F S L L K Q A G D V E E N P G P

E2A:
(SEQ ID NO: 8)
(GSG) Q C T N Y A L L K L A G D V E S N P G P

F2A:
(SEQ ID NO: 9)
(GSG) V K Q T L N F D L L K L A G D V E S N P G P c. Origins of Replication In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

d. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

e. Suicide Genes

The cells of the present disclosure that have been modified to harbor a vector encompassed by the disclosure may comprise one or more suicide genes. The term "suicide gene" as used herein is defined as a gene which, upon administration of a prodrug or other agent, effects transition of a gene product to a compound which kills its host cell. Examples of suicide gene/prodrug combinations which may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The E. coli purine nucleoside phosphorylase, a so-called suicide gene which converts the prodrug 6-methylpurine deoxyriboside to toxic purine 6-methylpurine, may be used. Other examples of suicide genes used with prodrug therapy are the E. coli cytosine deaminase gene and the HSV thymidine kinase gene.

Exemplary suicide genes include CD20, CD52, EGFRv3, or inducible caspase 9. In one embodiment, a truncated version of EGFR variant III (EGFRv3) may be used as a suicide antigen which can be ablated by Cetuximab. Further suicide genes known in the art that may be used in the present disclosure include Purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-α,γ-lyase (MET), and Thymidine phosphorylase (TP). In specific embodiments, a mutant TNF-alpha suicide gene is utilized that encodes for a non-secretable TNF alpha protein that is expressed on the cell membrane, allowing it to be targeted by an inhibitor, such as an antibody, as described in U.S. Provisional Patent Application 62/769,405, filed Nov. 19, 2018, and in U.S. Provisional Patent Application 62/773,372, filed Nov. 30, 2018, and in U.S. Provisional Patent Application 62/791,464, filed Jan. 11, 2019, all of which are incorporated by reference herein in their entirety.

IV. Methods of Treatment

In some embodiments, the present disclosure provides methods for therapy, including immunotherapy, comprising administering an effective amount of immune cells encompassed by the present disclosure that are engineered to express the CD8αβ co-receptor. In some embodiments, a medical disease or disorder is treated by transfer of the cells to a recipient individual. In certain embodiments of the present disclosure, cancer is treated by transfer of cell population that targets an antigen. Provided herein are methods for treating or delaying progression of cancer in an individual comprising administering to the individual an effective amount of antigen-specific cell therapy (specific to one or more antigens).

In cases where an individual in need of therapy has cancer, the cancer may be blood cancer or may comprise solid tumors. Tumors for which the present treatment methods are useful include any malignant cell type, such as those found in a solid tumor or a hematological malignancy. Exemplary solid tumors can include, but are not limited to, a tumor of an organ or tissue selected from the group consisting of pancreas, colon, cecum, stomach, brain, head, neck, ovary, kidney, larynx, sarcoma, lung, bladder, melanoma, prostate, skin, thyroid, gall bladder, spleen, liver, bone, endometrium, testes, cervix, esophagus, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL, bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

In certain embodiments of the present disclosure, transgenic CD4+ and/or CD8+ cells are delivered to an individual in need thereof, such as an individual that has cancer. The cells then enhance the individual's immune system to attack the respective cancer. In some cases, the individual is provided with one or more doses of the cells. In cases where the individual is provided with two or more doses of the cells, the duration between the administrations should be sufficient to allow time for propagation in the individual, and in specific embodiments the duration between doses is 1, 2, 3, 4, 5, 6, 7, or more days.

In certain embodiments, a growth factor that promotes the growth and activation of the cells is administered to the subject either concomitantly with the cells or subsequently to the cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of the cells can be administered by a number of routes, including parenteral administration, for example, intravenous, intraperitoneal, intramuscular, intrasternal, or intraarticular injection, or infusion.

The therapeutically effective amount of the modified CD4+ and/or CD8+ cells for use in adoptive cell therapy is that amount that achieves a desired effect in a subject being treated. For instance, this can be the amount of immune cells necessary to inhibit advancement, or to cause regression of cancer.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m². In a certain embodiment, the dose used in the treatment of human subjects ranges from about $3.8 \times 10^9$ to about $3.8 \times 10^{10}$ immune cells/m². In additional embodiments, a therapeutically effective amount of immune cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

V. Pharmaceutical Compositions

Also provided herein are pharmaceutical compositions and formulations comprising the modified CD4+ and/or CD8+ cells (e.g., T cells or NK cells) and a pharmaceutically acceptable carrier.

Pharmaceutical compositions and formulations as described herein can be prepared by mixing the active ingredients (such as the cells) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn– protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

VI. Combination Therapies

In certain embodiments, the compositions and methods of the present embodiments involve a modified CD4+ and/or CD8+ T cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

A cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy. Specific examples follow concerning embodiments wherein the individual has cancer.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma1I and calicheamicin omega1I); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169); cytokine therapy, e.g., interferons α, β and γ, IL-1, GM-CSF, and TNF; gene therapy, e.g., TNF, IL-1, IL-2, and p53 (U.S. Pat. Nos. 5,830,880 and 5,846,945); and monoclonal antibodies, e.g., anti-CD20, anti-ganglioside GM2, and anti-p185 (U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VII. Articles of Manufacture or Kits

An article of manufacture or a kit is provided comprising the CD4+ and/or CD8+ cells, or cells from which the CD4+ and/or CD8+ cells may be produced, is also provided herein. The article of manufacture or kit can further comprise a package insert comprising instructions for using the cells to treat or delay progression of cancer in an individual or to enhance immune function of an individual having cancer. Any of the antigen-specific cells described herein, or reagents to produce them, may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

EXAMPLES

The following examples are included to demonstrate particular embodiments of the disclosure. It should be appreciated by those of skill in the art that the techniques disclosed in the examples that follow represent techniques discovered by the inventor to function well in the practice of the methods of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1

Figure 1D:
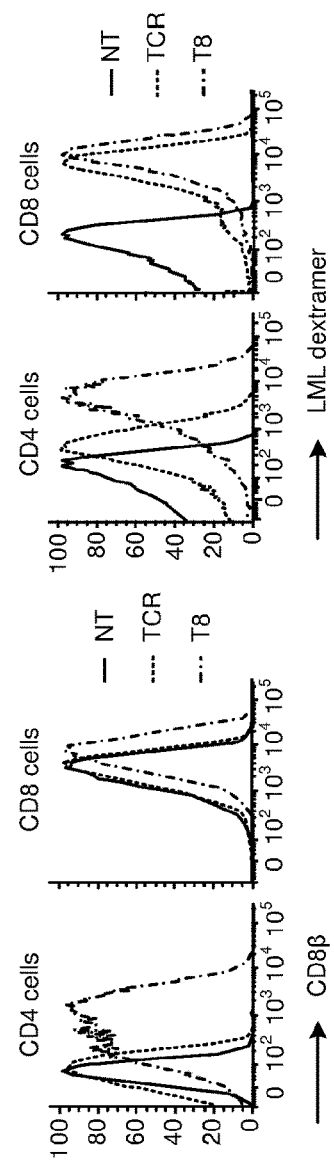
Figure 1E:
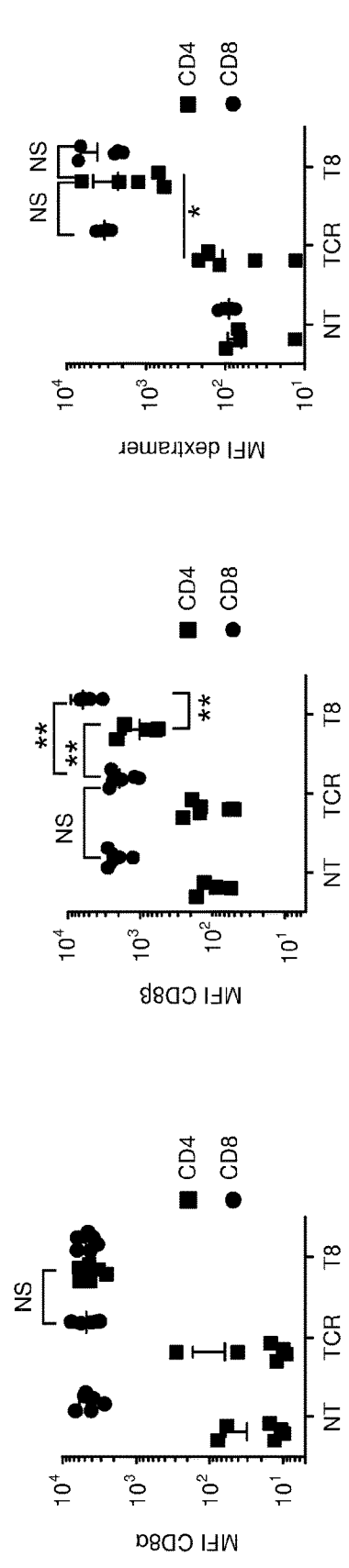

Harnessing CD8 Co-Receptor Function for Immunotherapy with Low-Avidity TCR Transgenic T Cells Co-transduction of a transgenic TCR and CD8αβ modifies both CD8+ and CD4+ T cell phenotypes. When isolated from autologous TCR repertoires, most TCRs targeting overexpressed tumor-associated self-antigens are characterized by low avidity and depend on the CD8 co-receptor.[2,11] Various types of measurements may be performed to characterize the TCR-peptide-MHC interactions.[30] To test whether transgenic CD8α- and CD8β-chains can be efficiently expressed from a polycistronic vector incorporating a tumor-targeted TCR, a retroviral vector was constructed coding for a survivin-specific TCR (s24), CD8αβ, and a selectable marker (ΔCD271) (T8, FIG. 1A), as well as vectors encoding for a TCR (survivin s24 and s16, PRAME p28 and pH) or CD8αβ alone. CD4+ and CD8+ selected T cells were transduced with s24-TCR or s24-T8 and analyzed for transduction efficiencies. Both CD4+ and CD8+ cells transduced equally well (% TCR+CD4 vs CD8: 82±9 vs 84±4, p=NS; % T8+CD4 vs CD8: 52±10 vs 45±8%, p=NS; n=6, mean±SD, FIG. 1B). But transduction efficiencies were significantly lower with the polycistronic T8 vector compared to TCR alone (CD4 TCR+vs T8+: p<0.001, CD8 TCR+vs T8+: p<0.001, n=6, FIG. 1B). In CD8+ T cells, CD8α levels were unchanged when comparing NT, TCR+ and T8+ cells (FIG. 1C). Interestingly, CD8β levels were significantly higher in T8+ compared to TCR+CD8+ T cells (CD8β MFI: $6.3±2.7×10^3$ vs $1.9±0.6×10^3$, n=7, mean±SD, p=0.008, FIG. 1D). In CD4+ T cells, co-transduction with CD8αβ produced a hybrid phenotype. CD8α cell surface levels in T8+CD4+ T cells were comparable to TCR+CD8+ T cells (CD8α MFI: $4.6±1.7×10^3$ vs $4.3±1.3×10^3$, n=6, mean±SD, p=NS) (FIG. 1C), but CD8β cell surface levels in T8+CD4+ T cells were significantly lower compared to TCR+CD8+ T cells (CD8β MFI: $1.0±0.6×10^3$ vs $1.9±0.6×10^3$, n=7, mean±SD, p=0.002). CD4+ T cells only recognized the targeted survivin epitope when CD8αβ was co-expressed with the TCR (Dextramer MFI, CD4 TCR+vs T8+: $0.1±0.08×10^3$ vs $2.3±2.5×10^3$, p=0.02; CD8 TCR+vs T8+: $3.4±0.6×10^3$ vs $4.2±2.6×10^3$, p=NS; n=5, mean±SD) (FIG. 1E). Dextramer binding was equivalent in TCR+ and T8+CD8+ T cells, and also comparable between T8+CD4+ T cells and TCR+CD8+ T cells (Dextramer MFI $2.3±2.5×10^3$ vs $3.4±0.6×10^3$, p=NS). Thus, forced expression of CD8αβ and a class I restricted TCR produced (1) CD8+ T cells with increased cell-surface levels of CD8β, and (2) hybrid CD4+ T cells with surface expression of CD8αβ-chains and the novel capacity to recognize and bind targeted pMHC class I complex, similar to native CD8+ T cells.

Figure 2:
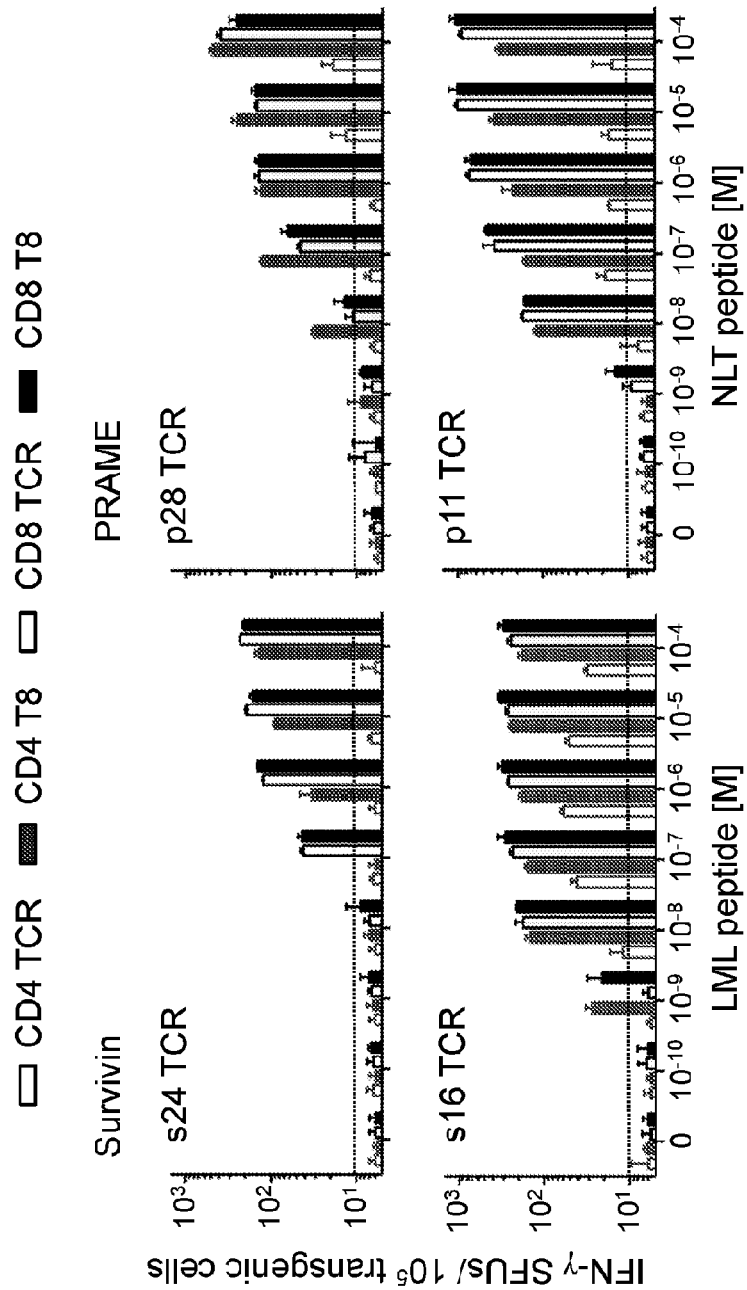
FIG. 2: T8+CD4+ T cells display similar functional avidity as TCR+ or T8+CD8+ T cells. Avidity of transgenic survivin specific (s24, top left; s16 bottom left) or PRAME-specific (p28, top right; p11, bottom right) TCR+(open bars) or T8+(solid bars) CD4+(red bars) or CD8+ T cells (black bars) against survivin LML or PRAME NLT peptide by IFN-γ ELISpots (SFUs/$10^5$ transgenic cells). Data from one representative donor is shown with 3 donors tested for each TCR. Detection limit: black dotted line.

T8+CD4+ T cells have a similar avidity for the targeted class I restricted epitope as TCR+ or T8+CD8+ T cells. To determine the effects of CD8αβ co-expression in selected CD8+ and CD4+ T cells, transgenic T cell avidity was measured using four different TCRs; two targeting the survivin ELT/LML epitope (s24 and s16) and two targeting the PRAME NLT epitope (p28 and p11). All TCR constructs used mouse constant regions to minimize cross-pairing with endogenous TCR chains (FIG. 1A), and transduction efficiencies were adjusted.[2] T cells were exposed to serial dilutions of the cognate peptides and resulting IFNγ ELIspots were counted. Co-transduction of CD8αβ did not affect CD8+ T cell avidity, however, it reprogrammed CD4+ T cells to recognize the targeted class I epitopes with similar avidity as CD8+ T cells (FIG. 2). At limiting peptide concentrations, and for all four TCRs tested, the number of IFN-γ spot forming units (SFUs) was similar in CD4+ T cells transduced with T8 compared to CD8+ T cells transduced with TCR alone. Hence, CD8 co-transfer can be used as a general strategy to redirect CD4+ T cells to a class I restricted epitope.

Co-expression of CD8αβ with TCR conveys sequential killing capacity to CD8+ and CD4+ T cells. T cells were co-cultured with survivin+HLA-A*02:01+BV173 leukemia cells at a low E:T ratio (1:5) and HLA class I restricted target cell killing was assessed. As expected, TCR+ and T8+CD8+ T cells readily killed their targets. CD4+ T cells only killed when transduced with T8, but not with TCR alone, and killing by T8+CD4+ T cells was equivalent to TCR+ or T8+CD8+ T cells (CD4: T8+ vs TCR+, p=0.0004; T8+CD4 vs TCR+CD8 or T8+CD8, p=NS, n=7) (FIG. 3A) This cytotoxicity was HLA class I restricted, as TCR+ or T8+CD8+ T cells only killed wild type but not B2M-KO BV173 cells (FIG. 3B) that are surface HLA-A*02:01 negative. The same effect was observed with T8+CD4+ T cells. To assess if the anti-tumor function would rapidly become exhausted when tumor burdens were high, the inventors challenged CD8+ and CD4+ T cells transduced with TCR, T8 or NT controls up to four times with fresh survivin+HLA-A*02:01+BV173 leukemia cells at low E:T ratios (FIG. 3C). Of note, there was a significantly increased serial tumor killing capacity for T8+CD8+ T cells compared to TCR+(number of killings T8+ vs TCR+2±1.4 vs 1.3±1.1, p=0.04, n=7, FIG. 3D, upper right panel). CD4+ T cells only killed when transduced with T8 but not with TCR alone (number of killings T8+ vs TCR+: 3.3±0.5 vs 0±0, p<0.0001, n=7, FIG. 3D, upper left panel), and T8+CD4+ T cells were as efficient at serial killing as T8+CD8+ T cells (number of killings T8+CD4 vs CD8: 3.3±0.5 vs 2±1.4, p=NS, n=7). Lastly, forced expression of CD8αβ also resulted in modified T cell expansion over multiple tumor challenges (FIG. 3D, lower panels, dotted lines). CD8+ T cell expansion was not significantly changed after CD8αβ co-transfer (CD8 TCR+vs T8+: p=NS, t-test on log AUC). However, T8+CD4+ T cells expanded significantly better than TCR+CD4+ T cells (p<0.0001), TCR+CD8+ T cells (p<0.002) and T8+CD8+ T cells (p<0.02).

Figure 3F:
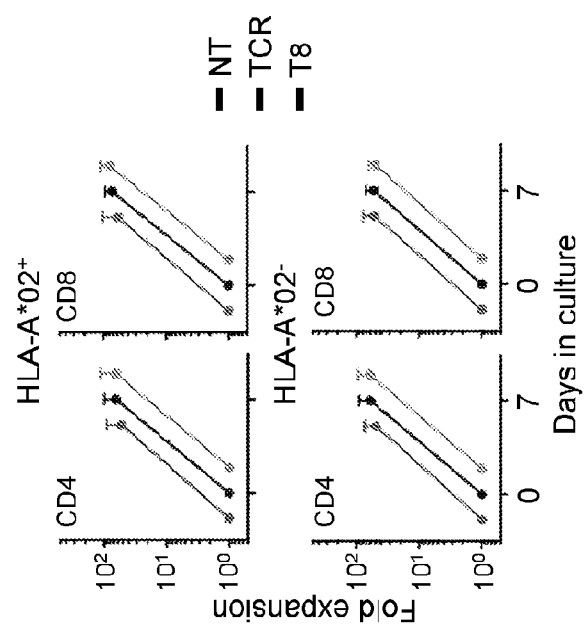

To further characterize the cytotoxic phenotype produced by CD8αβ co-transfer, cytokine production was examined in 24-hour co-culture supernatants after initial plating (D1) and after the third tumor challenge (D10). The cytokine production profile was not significantly altered in TCR+ versus T8+CD8+ T cells. However, CD8αβ co-transfer to CD4+ T cells produced a $T_H1$ predominant cytotoxic cytokine pattern. T8+CD4+ T cells secreted multiple cytotoxic cytokines including IFNγ, TNFα, perforin, or granzyme B, with levels comparable to TCR+ or T8+CD8+ T cells (FIG. 3E). In addition, only T8+CD4+ T cells produced some $T_H2$ cytokines, such as IL10 (FIG. 3E). Thus, cytotoxic CD8+ T cell function is enhanced by co-transfer of TCR and CD8αβ, while forced expression of CD8αβ imparts cytotoxic function to TCR+CD4+ T cells and preserves their natural helper function. Furthermore, T cell expansion in HLA-A*02+ and A*02-donors was comparable with all constructs (FIG. 3F), indicating that CD8 co-transfer did not increase the probability of producing TCR mediated on-target toxicity in activated T cells by low levels of endogenous survivin expression (also called fratricide).[4]

Figure 4A:
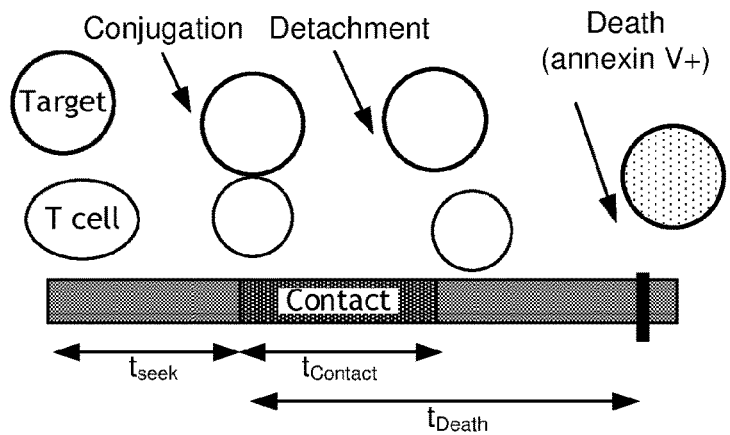
FIGS. 4A-4B: TCR-CD8αβ co-expression improves sequential killing capacity of single CD8+ T cells and converts single CD4+ T cells to cytotoxic CD8+ T cells.
Figure 4B:
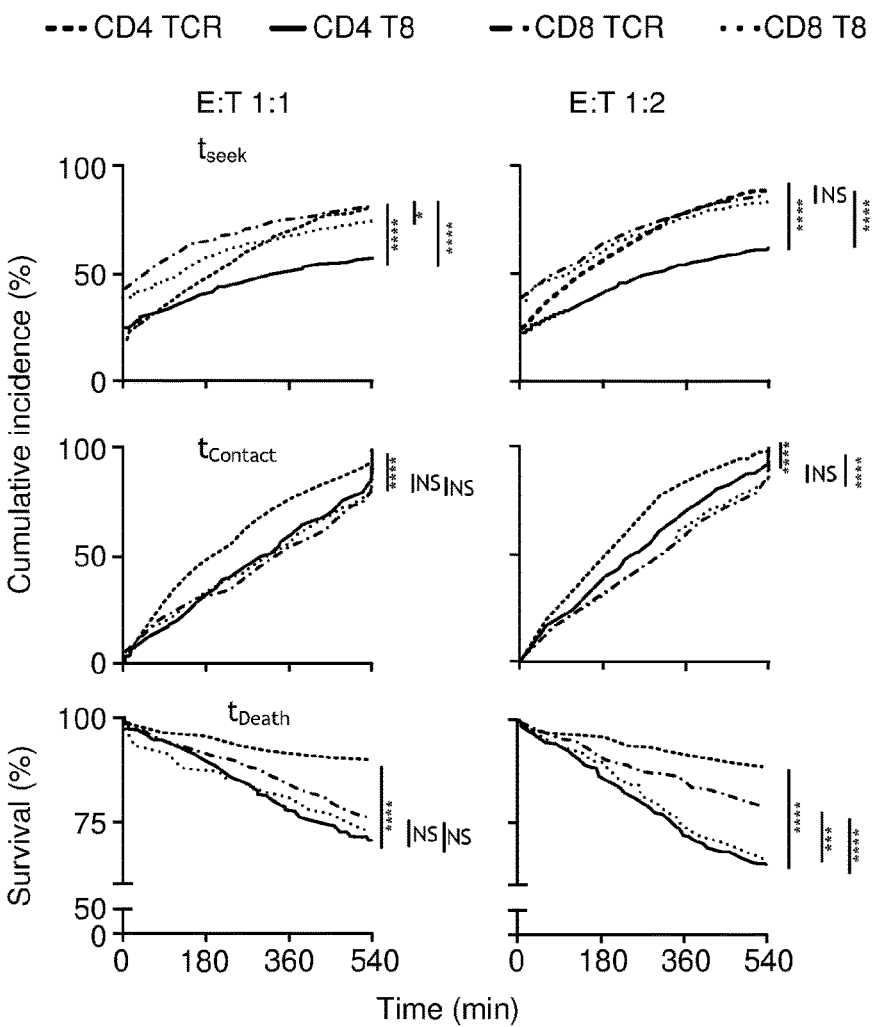
Figure 5A:
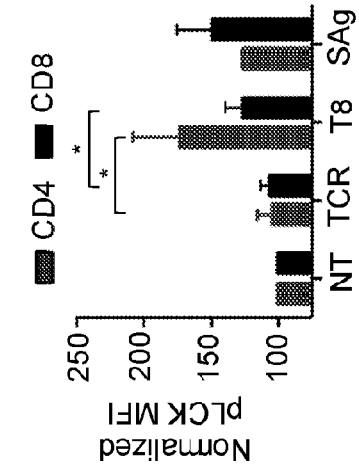
FIGS. 5A-5B: Analysis of early TCR signaling events.
Figure 5B:
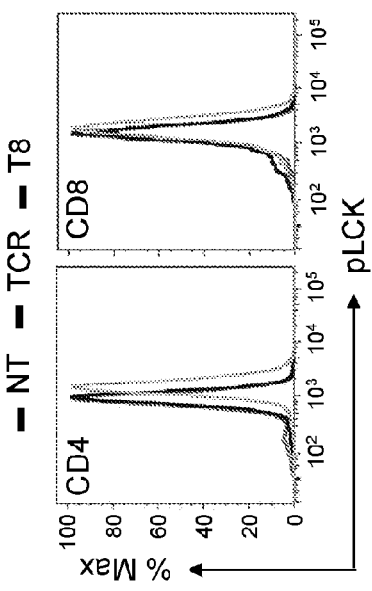

TCR-CD8αβ expression improves sequential killing capacity of single CD8+ T cells and converts single CD4+ T cells into cytotoxic CD8+ T cells. To assess the influence of transgenic CD8αβ expression on killing kinetics of TCR transgenic CD8+ and CD4+ T cells at the single cell level, high-throughput time-lapse imaging microscopy was performed in nanowell grids (TIMING).[22] The time needed to establish a stable conjugation with the target ($t_{Seek}$), the total duration of conjugation ($t_{Contact}$) and the time between first contact and tumor cell apoptosis ($t_{Death}$) were measured over 9 hours (FIG. 4A). CD8+ T cells were efficient at finding their target and establishing a stable conjugation. TCR+ CD8+ T cells were more efficient than T8+CD8+ T cells at finding targets at E:T 1:1 (FIG. 4B top panels, $t_{Seek}$ CD8 TCR+vs T8+, p=0.01), but established equally stable contacts (FIG. 4B middle panels, $t_{Contact}$ p=NS). Their killing capacity was equivalent at E:T 1:1 (single T cell and single target cell per well, FIG. 4B bottom left, p=NS)), however, sequential killing capacity was significantly enhanced in T8+CD8+ T cells at E:T 1:2 (single T cell and two target cells per well, FIG. 4B bottom right, p=0.0002). As expected, TCR+CD4+ T cells were not able to form stable conjugates and kill the target cells, despite the fact that they were actively seeking targets and found contacts (FIG. 4B, $t_{Seek}$ and $t_{Contact}$, CD4: TCR+vs T8+; p<0.0001). However, T8+CD4+ T cells efficiently killed their targets. At E:T 1:1, T8+CD4+ T cells found, conjugated to and killed their target as efficiently as TCR+ or T8+CD8+ T cells (FIG. 4B, p=NS). At E:T 1:2, T8+CD4+ T cells killed as efficiently as T8+CD8+ T cells (FIG. 4B, bottom right, p=NS), and killed better than TCR+CD8+ T cells (FIG. 4B, bottom right, p<0.0001). From these TIMING assay results it is determined that (1) CD8αβ co-transfer in single CD8+ T cells significantly enhances the serial killing capacity, and (2) the single cell target seeking, conjugation and killing kinetics of T8+CD4+ T cells are comparable to TCR+ or T8+CD8+ T cells.

Transgenic CD8αβ enhances early TCR signaling events. To assess whether transgenic CD8αβ enhanced early TCR signaling events, the inventors analyzed Lck phosphorylation at the activating Y394 site after short stimulation of T cells with BV173 leukemia cells. Co-transfer of CD8αβ significantly increased activating pLCK Y394 levels in T8+CD8+ T cells as well as T8+CD4+ T cells (FIGS. SA and 5B), indicating that transgenic expression of the CD8 co-receptor not only provides stability to the TCR-pMHC complex but also enhances early TCR signaling events in both CD8+ and CD4+ T cell subsets.

Figure 6A:
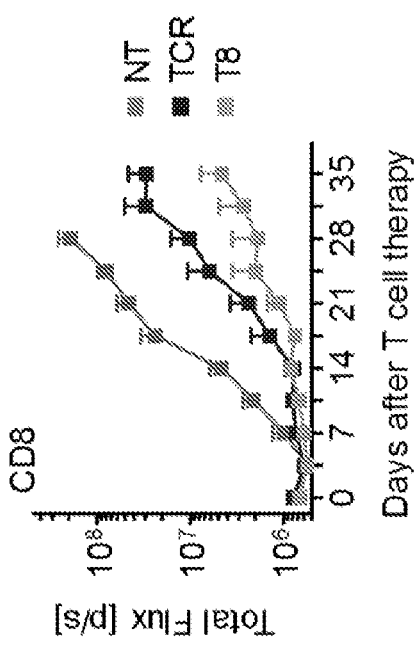
FIGS. 6A-6E: Transgenic CD8αβ enhances the in vivo anti-tumor function of TCR-transgenic CD8+ and CD4+ T cells.
Figure 6B:
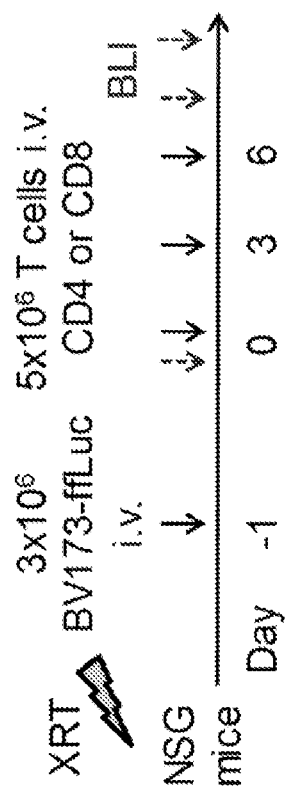
Figure 6C:
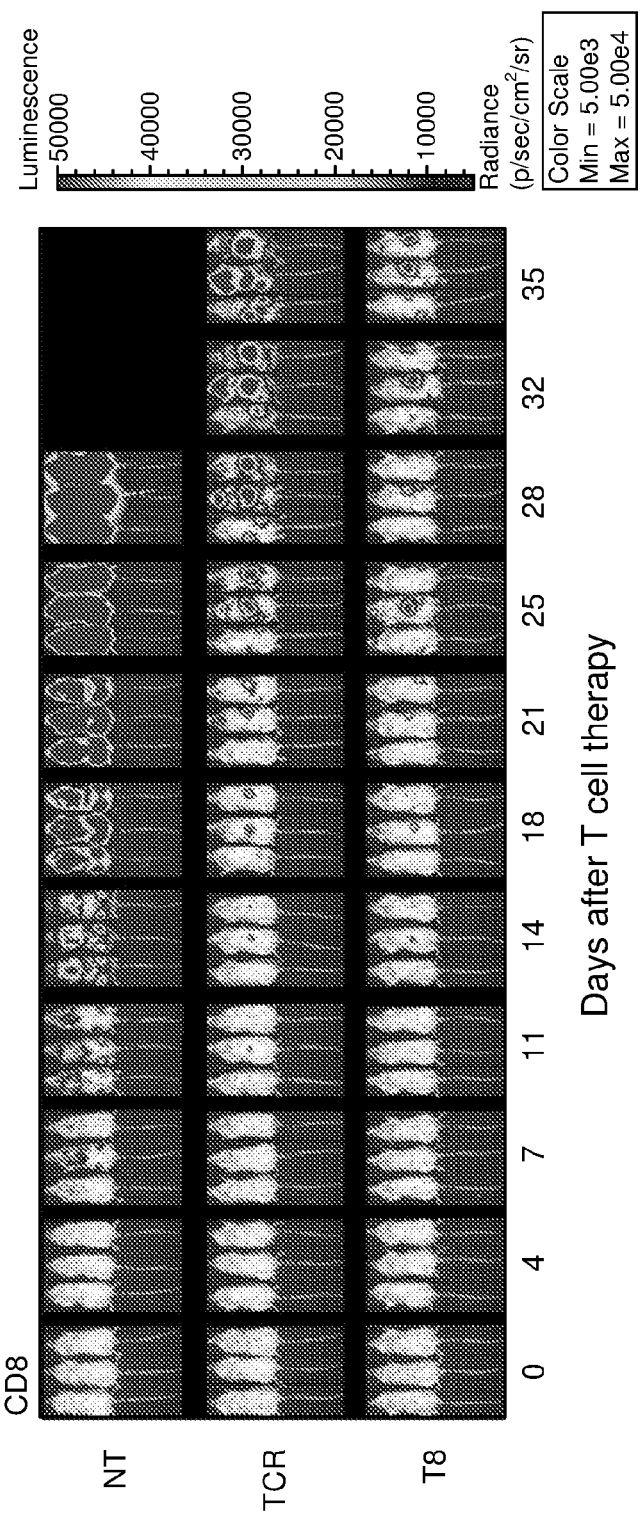
Figure 6D:
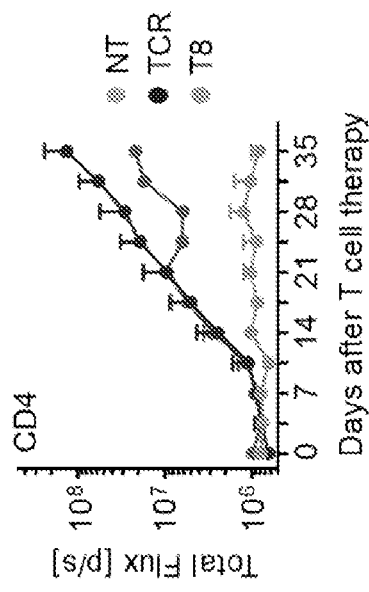
Figure 6E:
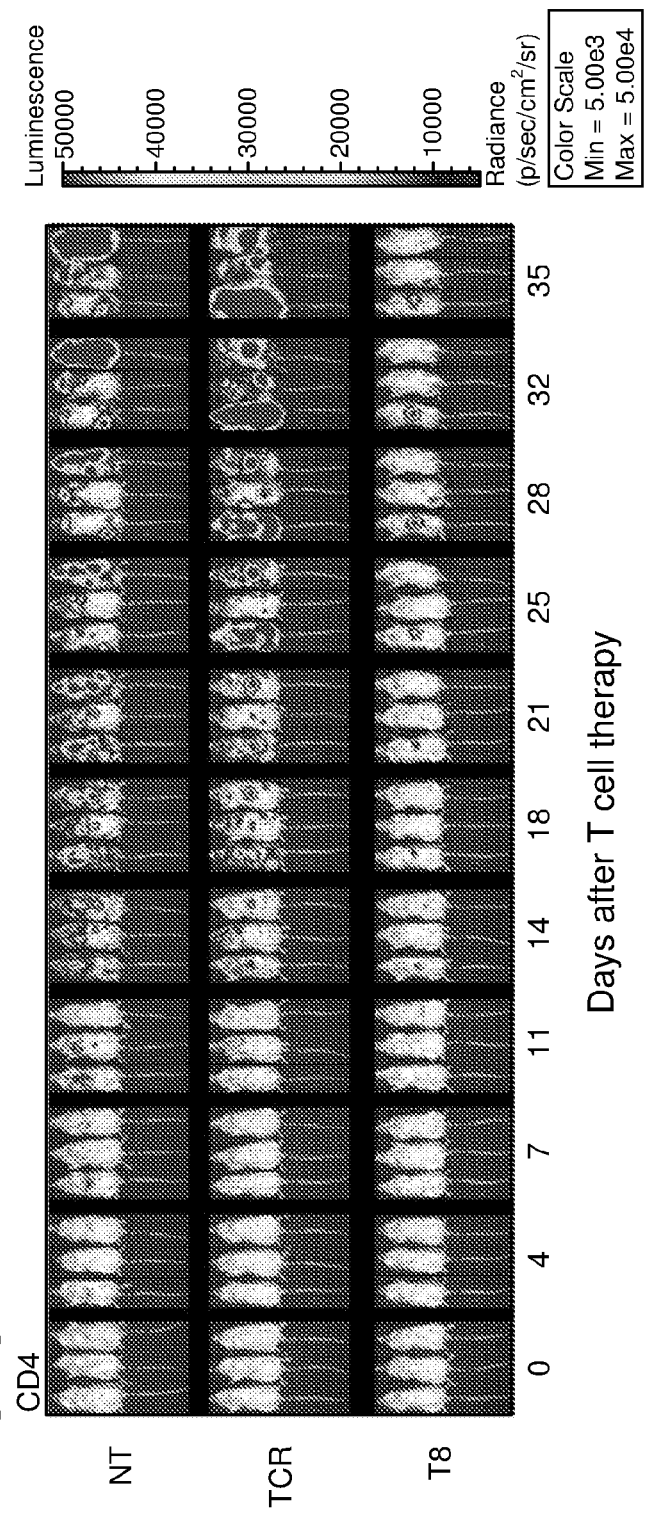

Transgenic CD8αβ enhances the in vivo anti-tumor function of TCR-transgenic CD8+ and CD4+ T cells. Finally, the in vivo anti-tumor function was tested of transgenic T cells in a previously established leukemia xenograft model with NSG mice engrafted with BV173.ffLuc leukemia cells.[2] In brief, sublethally irradiated NSG mice were injected i.v. with BV173.ffLuc cells, followed by three T cell infusions with NT, TCR or T8 transgenic CD8+ or CD4+ T cells (FIG. 6A). Tumor growth was measured by in vivo BLI. There was significant leukemia control in mice treated with TCR+CD8+ T cells compared to NT controls, and further enhancement in mice treated with T8+CD8+ T cells (FIGS. 6B and 6C, n=5/group, NT vs TCR: p=0.0002, NT vs T8: p<0.0001, TCR vs T8: p=0.01, t-test on log AUC on day 28 compared to day 0). As expected, neither NT control T cells nor TCR+CD4+ T cells controlled leukemia growth. In contrast T8+CD4+ T cells significantly delayed leukemia progression up to day 35 (FIGS. 6D and 6E, n=5/group, p=0.001, t-test on log AUC on day 35 compared to day 0). Thus, transgenic expression of CD8αβ together with a tumor-targeted class I TCR both enhances CD8+ T cell function and confers anti-tumor function to CD4+ T cells.

Significance of Certain Embodiments

With the goal of exploiting CD8 co-receptor functions and enhance adoptive T cell therapy with tumor-targeted HLA-class I restricted TCRs, the inventors explored the properties of purified CD8+ and CD4+ T cell populations, engineered to express TAA-specific TCRs alone or in combination with the CD8αβ co-receptor. The two main issues that were characterized were (1) whether CD8+ T cell function could be enhanced by increasing the availability of co-receptor molecules upon transduction with TCR and CD8αβ, and (2) whether transgenic co-expression of TCR and CD8αβ could redirect CD4+ T cells to the targeted class I epitope while preserving their T helper functions. It was determined that CD8 co-transfer enhanced cytotoxicity of CD8+ T cells in vitro and in vivo, including their sequential killing capacity. Transgenic CD4+ T cells displayed a hybrid phenotype with co-expression of CD4 and CD8, recognition of cognate antigen with similar avidity as native CD8+ T cells, and killed targets in a class I restricted manner. Hybrid CD4+ T cells readily killed leukemia cells in serial killing assays and at the single cell level, and produced cytotoxic as well as $T_H$ cytokines. Hybrid CD4+ T cells were also able to control leukemia growth in mouse xenografts.

Forced expression of class I restricted TAA-specific TCRs and adoptive T cell transfer is a successful therapeutic strategy for certain solid tumors and hematologic malignancies.[1,24,25] Most self-TAA specific TCRs are of low avidity and depend on the presence of the CD8 co-receptor, while only rare naturally occurring or ex vivo engineered TAA-specific TCRs with high avidities are CD8 independent[11,26,27] Thus, most adoptive transfer protocols rely on CD8+ T cells to produce the desired in vivo anti-tumor function. Physiologically, the CD8 co-receptor in its heterodimeric form (αβ) plays a major role in class I restricted antigen recognition and T cell activation in mature peripheral T cells. The two main functions are to stabilize the TCR-pMHC complex at the immunological synapse and to enhance early TCR signaling events by Lck Y394 phosphorylation in lipid rafts.[28,29] Transgenic TCRs thus rely on the cell's endogenous availability of CD8αβ co-receptor molecules for their function. It is contemplated herein that in specific embodiments the number of available CD8 molecules in CD8+ T cells may be a limiting factor for immunological synapse formation and anti-tumor function of TCR-transgenic CD8+ T cells because copy numbers of transgenic TCRs are supraphysiologic.[12] Thus, the functional consequences of co-receptor overexpression was assessed in CD8+ T cells equipped with low-avidity TAA-specific TCRs and found improved TCR-specific cytotoxicity, serial killing capacity and in vivo anti-tumor function upon correction of the TCR-CD8αβ molecule imbalance.

CD4+ T cells exert a great variety of functions in orchestrating efficient immune responses against infections and cancer, and their interplay with CD8+ T cells is of crucial importance,[13,14] as recently demonstrated by the adoptive transfer of CD4+$T_H$1 tumor infiltrating lymphocytes targeting tumor neoantigens, or by the infusion of CD19-CAR T cells with a defined ratio of CD4:CD8 T cells.[16,18] Thus, functional CD4+ T cells should likely be incorporated into TCR-transgenic T cell products for adoptive transfer, as CD4+ T cells can greatly contribute to tumor control and CD8+ T cell persistence after adoptive transfer. It was previously shown that CD8-independent class I restricted TCRs can efficiently be overexpressed in CD4+ T cells which produces multifunctional CD4+ T cells with both cytotoxic and helper cell functions, and the capacity to control tumor growth in vivo in xenograft models.[26,27] We therefore assessed whether transgenic CD8 co-expression could reprogram unresponsive CD4+T cells expressing low-avidity class I restricted TCRs into multifunctional hybrid T cells with both cytotoxic and helper functions. Indeed, CD8αβ co-expression in CD4+ T cells produced polyfunctional hybrid cytotoxic and helper cells with enhanced characteristics for adoptive transfer, including serial killing ability in vitro at the single cell level and leukemia control in vivo.

Selection of optimal TAA-specific TCRs for adoptive T cell therapy is a challenging task, as there is a fine line between optimal avidity to eliminate tumor cells and the potential to create off-target toxicities.[1,2,4,6-9] Because tumor-associated self-antigens are overexpressed in cancer but are also present at low levels in certain normal healthy tissues, on-target off-tumor toxicities can occur if the TCR avidity is too high and the TCR recognizes very low levels of pMHC presented on the cell surface. However, the strategy of the disclosure of stabilizing the TCR-pMHC interaction of low-avidity TAA-specific TCRs by co-expression of the CD8 co-receptor safely enhanced the overall TCR+ T cell to target cell interaction as no evidence for fratricide was seen in the T cell expansion cultures.

Overall, transgenic co-expression of the CD8αβ co-receptor has beneficial effects on the function of TCR transgenic CD8+ and CD4+ T cells in vitro and in vivo. CD4+ T cells can be reprogrammed into polyfunctional hybrid T cells by class I TCRs and CD8, with simultaneous cytotoxic effector functions and preserved native helper functions. The use of such hybrid cells for adoptive T cell transfer represents a novel strategy where both CD8 and CD4 functions are readily available at the single cell level.

Example 2

Examples of Materials and Methods

Cell lines. BV173 cells were purchased from the German Cell Culture Collection (DSMZ) and K562, CEM-T2 (TAP transporter deficient) and 293T were obtained from the American Type Culture Collection (ATCC) Cells were maintained in complete RPMI 1640 or IMDM media (Hyclone; Thermo Scientific) supplemented with 10 or 20% fetal bovine serum (FBS, Hyclone), 1% penicillin-streptomycin (Gibco), and 1% glutamax (Gibco). Beta-2 microglobulin knock-out (B2M-KO) BV173 cells were generated using the CRISPR/Cas9 technology as previously described.[1] In brief, a B2M single-guide RNA (sgRNA, 5'-GGCCACGGAGCGAGACAUCU-3' (SEQ ID NO:1), Synthego) and recombinant Cas9 protein (CP01, PNA Bio), 1 μg each, were mixed at room temperature and used to electroporate $0.15 \times 10^6$ BV173 cells (3 pulses of 1600V for 10 ms, Neon Transfection System, Invitrogen). Electroporated cells were expanded in antibiotic-free medium and FACS sorted to greater than 98% purity for HLA-A2 negative cells. For in vivo xenograft experiments, BV173 cells modified to express the firefly luciferase (BV173.ffLuc) cells were used as previously described.[2]

Blood samples from healthy donors. Buffy coats were obtained from de-identified healthy human volunteers at the Gulf Coast Regional Blood Center (Houston, TX, USA).

Generation of retroviral vectors and supernatant. Retroviral vectors expressing the HLA-A*02:01 restricted survivin ELTLGEFLKL epitope (SEQ ID NO:2) (s24 or s16) and PRAME NLTHVLYPV epitope (SEQ ID NO 3) (p11 or p28) specific TCRs have been previously described.[2] Genes encoding for the human CD8α (Uniprot P01732) and CD8β isoform 1 (βM1, Uniprot P10966-1) chains, separated by a 2A sequence, were synthesized by Geneart (Invitrogen). They were either cloned as such into the SFG retroviral vector backbone or in combination with the s24 survivin-specific TCR, resulting in a polycystronic vector expressing all four genes, separated by different 2A sequences (FIG. 1) (In-Fusion HD Cloning Kit, Clontech). Transient retroviral supernatant was prepared by transfection of 293 T as described.[3]

Generation of transgenic T cells. Peripheral blood mononuclear cells (PBMCs) were isolated from buffy coats using density gradient centrifugation by Lymphoprep (Accurate Chemical and Scientific Corporation). Polyclonal CD4 and CD8 T cells were positively selected from PBMCs with microbeads (Miltenyi Biotech or StemCell Technologies) and activated in non-tissue culture treated 24-well plates (Corning) coated with OKT3 (purified from hybridoma CRL-8001; ATCC) and anti-CD28 antibody (BD Biosciences), and IL7 and IL15 (10 ng/mL each, R&D Systems) for 3 days, and transduced as described.[3] Cells were expanded for 7-10 days after retroviral transduction in IL7 and IL15 before used in experiments. T cells were cultured in a 1:1 mixture of RPMI 1640 and Click's media (Hyclone), complete with 10% FBS, 1% penicillin/streptomycin and 1% Glutamax.

Immunophenotyping. Cells were surface stained with FITC-, phycoerythrin (PE-), allophycocyanin (APC), V450-, or Krome Orange-conjugated antibodies (Abs) against CD4, CD8, CD271, CD19 (all BD Biosciences), FITC or APC conjugated murine TCR β constant region (ebiosciences, clone #H57-597) or PE-conjugated LML survivin-specific dextramer (Immudex) for 30 min at 4° C. 7-AAD (BD Biosciences) was used to exclude dead cells. To evaluate LCK phosphorylation, T cells were stimulated with BV173 cells (1:1 ratio) or Staphylococcus aureus enterotoxin B (0.1 μg/ml, Millipore Sigma, as a positive control) for 30 min at 37° C. Indirect intracellular staining was performed using anti-human phospho-LCK (Y394) (clone #755103) and anti-mouse IgG-NL557 Abs (R&D Systems) according to manufacturer's recommendations. Samples were acquired on a FACSCanto with BD FACSDiva software and analyzed with FlowJo software (Tree Star Inc.)

Peptides and IFN-γ ELISpot. The survivin ELTLGEFLKL ((SEQ ID NO:2), its heteroclitic variant LMLGEFLKL (SEQ ID NO:4) and the PRAMS NLTHVLYPV (SEQ ID NO:5) peptides were obtained from Genemed Synthesis. T cells ($10^5$) were plated in triplicates and stimulated 1:1 with peptide pulsed CEM-T2 cells, using serial dilutions of cognate peptide ($10^{-4}$ to $10^{-10}$M), with BV173 cells or media alone. Plates were incubated at 37° C./5% $CO_2$ over-night and developed as previously described.[2] Spot Forming Units (SFU) were enumerated by ZellNet.

Sequential co-culture assay. T cells and BV173 cells were co-cultured in four replicate wells at E:T ratio of 1:5 with no exogenous cytokines. Co-culture supernatants were harvested 24 h after initial plating and stored at −80° C. for cytokine analysis. Every 3-4 days of co-culture, remaining T cells and BV173 cells were enumerated by FACS and CountBright Beads (Life Technologies). To assess the sequential killing ability of remaining T cells, fresh BV173 cells ($1 \times 10^6$) were added back to untouched replicate wells if less than $1 \times 10^5$ residual tumor cells remained per well.

Cytokine multiplex assay. Cytokine concentrations in co-culture supernatants were quantified in duplicates using the MILLIPLEX Human CD8+ T-cell Magnetic Bead Panel (EMD Millipore) and analyzed with the Luminex 200 instrument (Luminex).

Timelapse imaging microscopy in nanowell grids (TIMING). The fabrication of nanowell arrays and the single-cell cytotoxicity assay were performed as described previously.[5,6] Briefly, the nanowell array was fixed on a 50-mm glass-bottom Petri dish (Ted Pella). T cells (effector) and BV173 cells (target) were labeled with PKH67 Green and PKH26 Red dyes (2 μM, Sigma-Aldrich) respectively. Effectors and targets were then loaded sequentially onto nanowell arrays ($10^6$ cells/mL) and the array was incubated at 37° C./5% $CO_2$, in phenol-red free media containing Annexin V-Alexa Fluor 647 (Invitrogen). The cells were monitored using Axio Observer (Carl Zeiss) fitted with Hamamatsu digital scientific CMOS camera using a 20×0.8 NA objective for 9 h at 5-min intervals. The images were processed using a combination of manual tracking and the implementation of an in-house algorithm for cell tracking and segmentation.[7]

Mouse xenograft model. Female NOD-SCID-γc$^{-/-}$ (NSG) mice (6-8 weeks old) were purchased from the Jackson Laboratory and housed at the Baylor College of Medicine Animal Facility. Sublethally irradiated (120 cGy) mice were infused intravenously (tail vein) with 3×10$^6$BV173.ffluc cells/mouse 4-6 h later. Leukemia burden was monitored by bioluminescent imaging (BLI) (photons/second/cm$^2$/sr) using the Xenogen in vivo imaging system (IVIS) (Caliper Life Sciences). Three T cell infusions (5×10$^6$ transgenic cells or controls/mouse, every 2-3 days) were administered i.v. (tail vein or retroorbital) beginning 24 h after tumor injection. Leukemia growth was monitored weekly by BLI.

Statistics. Data were summarized using descriptive statistics. Areas under the curves (AUCs) were calculated using trapezoidal rule for T-cell frequencies and bioluminescent intensity over time. Comparisons were made between groups using Wilcoxon rank-sum test or t-test, whichever is appropriate, for continuous variables. Normality assumption was examined and log transformation was performed if necessary to achieve normality. Survival analysis was carried out using the Kaplan-Meier method. The Wilcoxon test was used to assess statistically significant differences between groups of mice. The log-rank test was used to analyze TIMING assay results. GraphPad Prism 5 software (GraphPad software, Inc., La Jolla, CA), SAS 9.4 and R 3.3.2 were used for statistical analysis. P values<0.05 were considered statistically significant.

Study approval. All animal studies were reviewed and approved by the IACUC of Baylor College of Medicine

REFERENCES FOR THE PRESENT EXAMPLE ARE AS FOLLOWS

1. Gundry M C, Brunetti L, Lin A, et al. Highly Efficient Genome Editing of Murine and Human Hematopoietic Progenitor Cells by CRISPR/Cas9 *Cell Rep.* 2016; 17(5): 1453-1461.
2. Arber C, Feng X, Abhyankar H, et al. Survivin-specific T cell receptor targets tumor but not T cells. *J Clin Invest.* 2015; 125(1):157-168.
3. Nishimura C D, Brenner D A, Mukherjee M, et al. c-MPL provides tumor-targeted T-cell receptor-transgenic T cells with costimulation and cytokine signals. *Blood.* 2017; 130(25):2739-2749.
4. Hebeisen M, Schmidt J, Guillaume P, et al. Identification of Rare High-Avidity, Tumor-Reactive CD8+ T Cells by Monomeric TCR-Ligand Off-Rates Measurements on Living Cells. *Cancer Res.* 2015; 75(10):1983-1991.
5. Romain G, Senyukov V, Rey-Villamizar N, et al. Antibody Fc engineering improves frequency and promotes kinetic boosting of serial killing mediated by NK cells. *Blood.* 2014; 124(22):3241-3249.
6. Liadi I, Singh H, Romain G, et al. Individual Motile CD4(+) T Cells Can Participate in Efficient Multikilling through Conjugation to Multiple Tumor Cells. *Cancer Immunol Res.* 2015; 3(5):473-482.
7. Merouane A, Rey-Villamizar N, Lu Y, et al. Automated profiling of individual cell-cell interactions from high-throughput time-lapse imaging microscopy in nanowell grids (TIMING). *Bioinformatics.* 2015; 31(19):3189-3197.

REFERENCES

Any of the references herein, to the extent that they provide exemplary procedural or other details supplementary to those set forth herein, are specifically incorporated herein by reference.

1. Rapoport A P, Stadtmauer E A, Binder-Scholl G K, et al. NY-ESO-1-specific TCR-engineered T cells mediate sustained antigen-specific antitumor effects in myeloma. *Nat Med.* 2015; 21(8):914-921.
2. Arber C, Feng X, Abhyankar H, et al. Survivin-specific T cell receptor targets tumor but not T cells. *J Clin Invest.* 2015; 125(1):157-168.
3. Cho J H, Sprent J. TCR tuning of T cell subsets. *Immunol Rev.* 2018; 283(1):129-137.
4. Leisegang M, Wilde S, Spranger S, et al. MHC-restricted fratricide of human lymphocytes expressing survivin-specific transgenic T cell receptors. *J Clin Invest.* 2010; 120(11):3869-3877.
5. Li Y, Moysey R, Molloy P E, et al. Directed evolution of human T-cell receptors with picomolar affinities by phage display. *Nat Biotechnol.* 2005; 23(3):349-354.
6. Robbins P F, Li Y F, El-Gamil M, et al. Single and dual amino acid substitutions in TCR CDRs can enhance antigen-specific T cell functions. *J Immunol.* 2008; 180 (9):6116-6131.
7. Linette G P, Stadtmauer E A, Maus M V, et al. Cardiovascular toxicity and titin cross-reactivity of affinity-enhanced T cells in myeloma and melanoma. *Blood.* 2013; 122(6):863-871.
8. Cameron B J, Gerry A B, Dukes J, et al. Identification of a Titin-derived HLA-A1-presented peptide as a cross-reactive target for engineered MAGE A3-directed T cells. *Sci Transl Med.* 2013; 5(197):197ra103.
9. Morgan R A, Chinnasamy N, Abate-Daga D, et al. Cancer regression and neurological toxicity following anti-MAGE-A3 TCR gene therapy. *J Immunother* 2013; 36(2): 133-151.
10. Cole D K, Laugel B, Clement M, Price D A, Wooldridge L, Sewell A K. The molecular determinants of CD8 co-receptor function. Immunology. 2012; 137(2):139-148.
11. Hebeisen M, Schmidt J, Guillaume P, et al. Identification of Rare High-Avidity, Tumor-Reactive CD8+ T Cells by Monomeric TCR-Ligand Off-Rates Measurements on Living Cells. *Cancer Res.* 2015; 75(10):1983-1991.
12 Nishimura C D, Brenner D A, Mukherjee M, et al c-MPL provides tumor-targeted T-cell receptor-transgenic T cells with costimulation and cytokine signals. *Blood.* 2017; 130(25):2739-2749.
13. Ostroumov D, Fekete-Drimusz N, Saborowski M, Kuhnel F, Woller N. CD4 and CD8 T lymphocyte interplay in controlling tumor growth. *Cell Mol Life Sci.* 2018; 75(4): 689-713.
14. Kennedy R, Celis E. Multiple roles for CD4+ T cells in anti-tumor immune responses. *Immunol Rev.* 2008; 222: 129-144.
15. Walter E A, Greenberg P D, Gilbert M J, et al. Reconstitution of cellular immunity against cytomegalovirus in recipients of allogeneic bone marrow by transfer of T-cell clones from the donor. *N Engl J Med.* 1995; 333(16): 1038-1044.
16. Tran E, Turcotte S, Gros A, et al. Cancer immunotherapy based on mutation-specific CD4+ T cells in a patient with epithelial cancer. *Science.* 2014; 344(6184):641-645.
17. Sommermeyer D, Hudecek M, Kosasih P L, et al. Chimeric antigen receptor-modified T cells derived from defined CD8+ and CD4+ subsets confer superior antitumor reactivity in vivo. *Leukemia.* 2016; 30(2):492-500.
18. Turtle C J, Hanafi L A, Berger C, et al. Immunotherapy of non-Hodgkin's lymphoma with a defined ratio of CD8+ and CD4+CD19-specific chimeric antigen receptor-modified T cells. *Sci Transl Med.* 2016; 8(355): 355ra116.
19. Gundry M C, Brunetti L, Lin A, et al. Highly Efficient Genome Editing of Murine and Human Hematopoietic Progenitor Cells by CRISPR/Cas9. *Cell Rep.* 2016; 17(5): 1453-1461.
20. Romain G, Senyukov V, Rey-Villamizar N, et al. Antibody Fc engineering improves frequency and promotes kinetic boosting of serial killing mediated by N K cells. *Blood.* 2014; 124(22):3241-3249.
21. Liadi I, Singh H, Romain G, et al. Individual Motile CD4(+) T Cells Can Participate in Efficient Multikilling through Conjugation to Multiple Tumor Cells. *Cancer Immunol Res.* 2015; 3(5):473-482.
22. Merouane A, Rey-Villamizar N, Lu Y, et al. Automated profiling of individual cell-cell interactions from high-throughput time-lapse imaging microscopy in nanowell grids (TIMING). *Bioinformatics.* 2015; 31(19):3189-3197.
23. Hebeisen M, Allard M, Gannon P O, Schmidt J, Speiser D E, Rufer N. Identifying Individual T Cell Receptors of Optimal Avidity for Tumor Antigens. *Front Immunol.* 2015; 6:582.
24. Morgan R A, Dudley M E, Wunderlich J R, et al. Cancer regression in patients after transfer of genetically engineered lymphocytes. *Science.* 2006; 314(5796):126-129.
25. Robbins P F, Morgan R A, Feldman S A, et al. Tumor regression in patients with metastatic synovial cell sarcoma and melanoma using genetically engineered lymphocytes reactive with NY-ESO-1 *J Clin Oncol.* 2011; 29(7): 917-924.
26. Ray S, Chhabra A, Chakraborty N G, et al. MHC-I-restricted melanoma antigen specific TCR-engineered human CD4+ T cells exhibit multifunctional effector and helper responses, in vitro. *Clin Immunol.* 2010; 136(3): 338-347.
27. Frankel T L, Burns W R, Peng P D, et al. Both CD4 and CD8 T cells mediate equally effective in vivo tumor treatment when engineered with a highly avid TCR targeting tyrosinase. *J Immunol.* 2010; 184(11): 5988-5998.
28. Kabouridis P S. Lipid rafts in T cell receptor signalling. *Mol Membr Biol.* 2006; 23(1):49-57.
29. Laugel B, Cole D K, Clement M, Wooldridge L, Price D A, Sewell A K. The multiple roles of the CD8 coreceptor in T cell biology: opportunities for the selective modulation of self-reactive cytotoxic T cells. *J Leukoc Biol.* 2011; 90(6):1089-1099.
30. Hebeisen, M, Allard M, Gannon P O, Schmidt J, Speiser D E, and Rufer N. Identifying Individual T Cell Receptors of Optimal Avidity for Tumor Antigens. *Frontiers in Immunol.* 2015; 6(582):1-18.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of producing a CD4+ T cell having cytotoxic effector cell function and helper function for an individual, comprising transfecting a CD4+ T cell with a vector comprising a first nucleic acid (N1) encoding a CD8α, a second nucleic acid (N2) encoding a CD8β, a third nucleic acid (N3) encoding a T cell receptor (TCR)α, and a fourth nucleic acid (N4) encoding a TCRβ,
   wherein the TCRα and the TCRβ comprise an antigen binding portion that binds to an antigen, wherein the CD8α comprises the amino acid sequence SEQ ID NO: 11 and the CD8β comprises the amino acid sequence SEQ ID NO: 13,
   wherein the orientation of the nucleic acids on the vector is, from the 5' end to the 3' end, N4-N3-N1-N2,
   wherein the CD4+ T cell is autologous with respect to the individual.

2. The method of claim 1, wherein the N1, N2, N3, and N4 are separated by a 2A element or an IRES element.

3. The method of claim 2, wherein the N1, N2, N3, and N4 are separated by a 2A element.

4. The method of claim 2, wherein the N1, N2, N3, and N4 are separated by an IRES element.

5. The method of claim 1, wherein the antigen is a tumor antigen.

6. The method of claim 5, wherein the tumor antigen is selected from survivin.

7. The method of claim 1, wherein the vector is a viral vector or non-viral vector.

8. The method of claim 7, wherein the vector is a viral vector.

9. The method of claim 7, wherein the vector is a non-viral vector.

10. The method of claim 7, wherein the viral vector is an adenoviral vector, an adeno-associated viral vector, a retroviral vector, or a lentiviral vector.

11. The method of claim 10, wherein the vector is an adenoviral vector.

12. The method of claim 10, wherein the vector is an adeno-associated viral vector.

13. The method of claim 10, wherein the vector is a retroviral vector.

14. The method of claim 10, wherein the vector is a lentiviral vector.

* * * * *